(12) United States Patent
Jensen et al.

(10) Patent No.: US 8,362,072 B2
(45) Date of Patent: Jan. 29, 2013

(54) BRCA1-BASED BREAST OR OVARIAN CANCER TREATMENT AGENTS AND METHODS OF USE

(75) Inventors: Roy A. Jensen, Gardner, KS (US); Lisa M. Harlan-Williams, Lenexa, KS (US); Frank J. Schoenen, Lawrence, KS (US); Jeffrey Aube, Lawrence, KS (US); Gerald H. Lushington, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 13/525,831

(22) Filed: Jun. 18, 2012

(65) Prior Publication Data

US 2012/0259005 A1    Oct. 11, 2012

Related U.S. Application Data

(63) Continuation of application No. 12/270,252, filed on Nov. 13, 2008, now abandoned.

(60) Provisional application No. 60/987,935, filed on Nov. 14, 2007.

(51) Int. Cl.
    *A61K 31/34*    (2006.01)
(52) U.S. Cl. ........ 514/468; 514/461; 514/449; 514/183; 549/460; 549/458; 549/456; 549/429; 549/200
(58) Field of Classification Search .................. None
    See application file for complete search history.

(56) References Cited

U.S. PATENT DOCUMENTS

| | | | |
|---|---|---|---|
| 2003/0045546 A1 | 3/2003 | Cai et al. | 514/307 |
| 2010/0284964 A1 | 11/2010 | Cohen-Armon | 424/85.2 |

FOREIGN PATENT DOCUMENTS

| | | |
|---|---|---|
| JP | 2000-095767 | 4/2000 |
| WO | WO 2004/058253 | 7/2004 |
| WO | WO 2006/122150 | 11/2006 |
| WO | WO 2007/038669 | 4/2007 |

OTHER PUBLICATIONS

Bykov et al. "Restoration of the Tumor Suppressor Function to Mutant P53 by a Low-Molecular-Weight Compound" Nature Medicine 2002 8(3):282-288.

Hoshino et al. "Effects of *BRCA1* Transgene Expression on Murine Mammary Gland Development and Mutagen-Induced Mammary Neoplasia" International Journal of Biological Sciences 2007 3(5):281-291.

Yarden, R. I. and Papa, M. Z. "BRCA1 at the Crossroad of Multiple Cellular Pathways: Approaches for Therapeutic Interventions" Molecular Cancer Therapy 2006 5(6):1396-1404.

Yuli et al. "BRCA1a Has Antitumor Activity in TN Breast, Ovarian and Prostate Cancers" Oncogene 2007 26:6031-6037.

*Primary Examiner* — Anish Gupta
*Assistant Examiner* — Theodore R West
(74) *Attorney, Agent, or Firm* — Licata & Tyrrell P.C.

(57) ABSTRACT

A pharmaceutical composition for use in treating, inhibiting, and/or preventing breast and/or ovarian cancer can include: a molecule having a structure of one of Compounds 1-38, pharmaceutically acceptable salt thereof, or analog thereof; and a pharmaceutically acceptable carrier containing the compound. The pharmaceutically acceptable carrier can be configured for oral, systemic, transdermal, intranasal, suppository, parenteral, intramuscular, intravenous, or subcutaneous administration. The compound can be present in the composition in a therapeutically effective amount for treating, inhibiting, and/or preventing breast and/or ovarian cancer. Also, the compound can be present in a therapeutically effective amount for enhancing production of BRCA1.

9 Claims, 18 Drawing Sheets

BRCA1-BASED BREAST OR OVARIAN CANCER TREATMENT AGENTS AND METHODS OF USE

CROSS-REFERENCE TO RELATED APPLICATIONS

Figure 1:
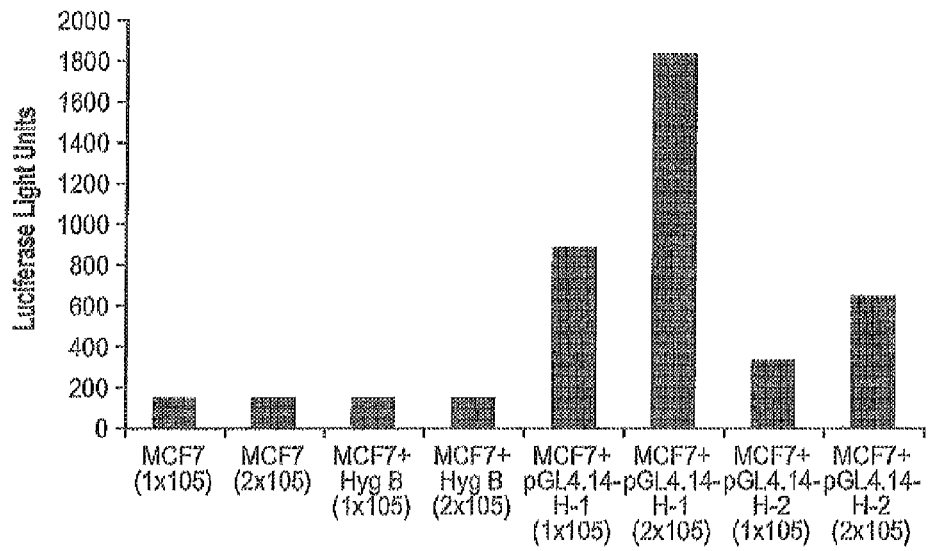

This patent application is a continuation application of U.S. patent application Ser. No. 12/270,252, filed Nov. 13, 2008 now abandoned, which claims benefit of U.S. Patent Application Ser. No. 60/987,935, filed Nov. 14, 2007, each of which are incorporated herein by specific reference in its entirety.

BACKGROUND

Cancer is one of the leading causes of death in the United States. Cancerous tumors result when a cell escapes from its normal growth regulatory mechanisms and proliferates in an uncontrolled manner. Tumor cells can metastasize to secondary sites if treatment of the primary tumor is either not complete or not initiated before substantial progression of the disease. Early diagnosis and effective treatment of tumors is, therefore, essential for survival.

Cancer involves the replication of populations of abnormal cells that have gained competitive advantage over normal cells through the alteration of regulatory genes. Regulatory genes can be broadly classified into "oncogenes" which, when activated or overexpressed, promote unregulated cell proliferation, and "tumor suppressor genes," which when inactivated or underexpressed, fail to prevent abnormal cell proliferation. Loss of function or inactivation of tumor suppressor genes is thought to play a central role in the initiation and progression of a significant number of human cancers.

Currently, breast and/or ovarian cancer are treated by surgery, radiation therapy, chemotherapy, targeted therapy, and hormonal therapy. To date, targeted therapies include trastuzumab and lapatinib, which target breast cancers that have increased HER2 receptors (HER2-positive). Bevacizumab targets the new blood vessels that feed cancer cells. Hormonal therapy blocks the ability of the hormone estrogen to stimulate the growth of breast cancer cells. Aromatase inhibitors, selective estrogen receptor modulators (SERMs), and estrogen-receptor down regulators are all different types of hormonal therapy currently available to breast cancer patients.

There are still many unsolved problems, disadvantages, and/or shortcomings that currently exist in the prevention and/or treatment of ovarian and/or breast cancer. Target therapies only work for HER2 positive breast cancers. However, only 15 to 20% of women with breast cancer have HER2-positive tumors. Hormonal therapy is an option for anyone with hormone receptor positive breast cancer. About 60% of breast cancers are hormone receptor positive. However, there are several side effects with hormonal therapy, including uterine cancer and weakening of the bones. Additionally, the side effects of current therapeutic regimens are treated as they appear in patients.

Additionally, mutations in one known tumor suppressor gene, breast cancer susceptibility to gene one (BRCA1), contribute in essentially all cases to inherited susceptibility to ovarian and breast cancers. Additionally, BRCA1 expression levels are reduced or undetectable in the tumor cells of sporadic breast cancers. In view of the importance of tumor suppressor molecules in the detection and treatment of cancer, and the known correlation of the tumor suppressor BRCA1 with breast and ovarian cancers, there exists a need to identify compounds that influence the level or activity of BRCA1.

Therefore, it would be beneficial to have a compound and method of use that will increase BRCA1 expression so as to delay and/or inhibit the onset of tumors. Such compounds and methods of use would be significant change in the treatment options for breast and ovarian cancer, as well as other cancers.

SUMMARY

In one embodiment, the present invention can include a pharmaceutical composition for use in treating, inhibiting, and/or preventing breast and/or ovarian cancer. Such a composition can include: a molecule having a structure of one of Compounds 1-38 (shown below), pharmaceutically acceptable salt thereof, or analog thereof; and a pharmaceutically acceptable carrier containing the compound. The pharmaceutically acceptable carrier can be configured for oral, systemic, transdermal, intranasal, suppository, parenteral, intramuscular, intravenous, or subcutaneous administration. The compound can be present in the composition in a therapeutically effective amount for treating, inhibiting, and/or preventing breast and/or ovarian cancer. Also, the compound can be present in a therapeutically effective amount for enhancing production of BRCA1.

In one embodiment, the present invention can include a compound or pharmaceutical composition having the compound for use in treating, inhibiting, and/or preventing breast and/or ovarian cancer. The composition can include: a compound having one of Formula B, Formula C, or pharmaceutically acceptable salt thereof that enhances production of BRCA1; wherein: X is independently selected from C, N, NH, N-alkyl, O, or S; Y is selected from C, or N; $R^1$ is a substituted or unsubstituted heterocycle selected from 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3)oxadiazole, 5-(1,2,3)oxadiazole, 4-(1,2,3)triazole, 5-(1,2,3)triazole, or 2-(1,3,4)thiadiazole, where the substituted heterocycle is substituted at any position with H, a halogen, Cl, F, $CH_3$, $CH_3CH_2$, or higher or lower substituted or unsubstituted straight chain or branched aliphatic; $R^2$ is a substituted or unsubstituted cycle or heterocycle selected from phenyl, 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3)oxadiazole, 5-(1,2,3)oxadiazole, 4-(1,2,3)triazole, 5-(1,2,3)triazole, or 2-(1,3,4)thiadiazole, where the substituted cycle or heterocycle is substituted at any position with H, a halogen, Cl, F, $CH_3$, $CH_3CH_2$, or higher or lower substituted or unsubstituted straight chain or branched aliphatic; Z is an amide, amine, imine, urea, thiourea, or thioamide functional group (either constitutional isomer, where possible); and n=0, 1, 2, or 3. The compound can be present in a therapeutically effective amount for enhancing production of BRCA1.

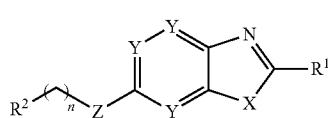

Formula B

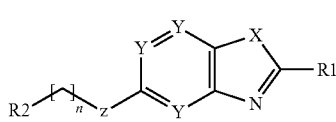

Formula C

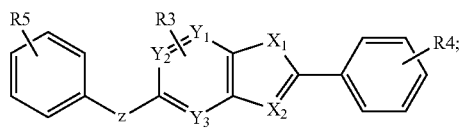

Formula F

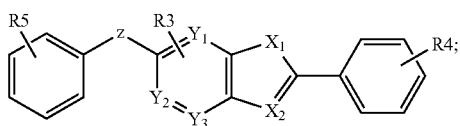

Formula G

The composition can include: a compound having one of Formula D, Formula E, or pharmaceutically acceptable salt thereof that enhances production of BRCA1; wherein: $X_1$ and $X_2$ are independently selected from C, N, NH, N-alkyl, O, or S; $Y_1$, $Y_2$, and $Y_3$ are independently selected from C, or N; $R^1$ is a substituted or unsubstituted heterocycle selected from 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3)oxadiazole, 5-(1,2,3)oxadiazole, 4-(1,2,3)triazole, 5-(1,2,3)triazole, or 2-(1,3,4)thiadiazole; $R^2$ is a substituted or unsubstituted cycle or heterocycle selected from phenyl, 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3)oxadiazole, 5-(1,2,3)oxadiazole, 4-(1,2,3)triazole, 5-(1,2,3)triazole, or 2-(1,3,4)thiadiazole; $R^3$ is a substituent on any one or more ring atoms independently selected from H, a halogen, Cl, F, Br, $NO_2$, $CH_3$, $CH_3CH_2$, or higher or lower substituted or unsubstituted straight chain or branched aliphatic; Z is an amide, amine, imine, urea, thiourea, or thioamide functional group (either constitutional isomer, where possible); and n=0, 1, 2, or 3; where $X_1$ and $X_2$ are not both N-alkyl, O, S, or O and S together, N-alkyl and O together, or N-Alkyl and S together. Optionally, the compound is not one of Compounds 1-32. The compound can be present in a therapeutically effective amount for enhancing production of BRCA1.

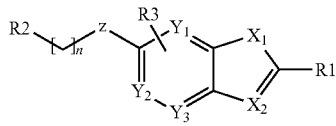

Formula D

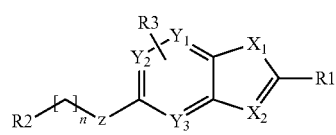

Formula E

The composition can have Formula F, Formula G, or pharmaceutically acceptable salt thereof that enhances production of BRCA1; where: $X_1$ and $X_2$ are independently selected from C, N, NH, N-alkyl, O, or S; $Y_1$, $Y_2$, and $Y_3$ are independently selected from C, or N; $R^3$, $R^4$, and $R^5$ are each a substituent on any one or more ring atoms independently selected from H, a halogen, Cl, F, Br, $NO_2$, $CH_3$, $CH_3CH_2$, or higher or lower substituted or unsubstituted straight chain or branched aliphatic; Z is an amide, amine, imine, urea, thiourea, or thioamide functional group (either constitutional isomer, where possible); and n=0, 1, 2, or 3; where $X_1$ and $X_2$ are not both N-alkyl, O, S, or O and S together, N-alkyl and O together, or N-Alkyl and S together.

The composition can have one of Formula H, Formula I, or pharmaceutically acceptable salt thereof that enhances production of BRCA1; where: $X_1$ and $X_2$ are independently selected from C, N, NH, N-alkyl, O, or S; $Y_1$, $Y_2$, and $Y_3$ are independently selected from C, or N; $Y_4$ is selected from C, N, NH, N-alkyl, O, or S; $R^3$ and $R^5$ are each a substituent on any one or more ring atoms independently selected from H, a halogen, Cl, F, Br, $NO_2$, $CH_3$, $CH_3CH_2$, or higher or lower substituted or unsubstituted straight chain or branched aliphatic; Z is an amide, amine, imine, urea, thiourea, or thioamide functional group (either constitutional isomer, where possible); and n=0, 1, 2, or 3; where $X_1$ and $X_2$ are not both N-alkyl, O, S, or O and S together, N-alkyl and O together, or N-Alkyl and S together.

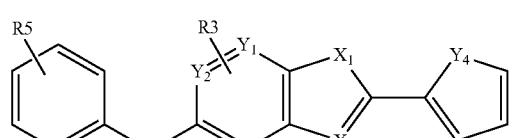

Formula H

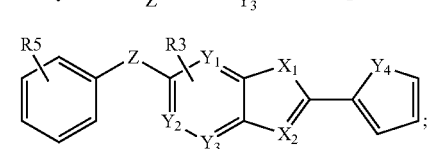

Formula I

In one embodiment, the present invention can include a method of treating, inhibiting, and/or preventing breast and/or ovarian cancer. Such a method can include: providing a compound as described herein (e.g., compounds 1-38 and/or Formulas A-I); and administering a therapeutically effective amount of the compound to a subject so as to increase BRCA1 production. The increased BRCA1 production can be sufficient to inhibit the growth and/or propagation of breast and/or ovarian cancer cells. The increased BRCA1 production can be increased compared to BRCA1 production in the subject prior to being administered the compound.

In one embodiment, the present invention can include a method of increasing BRCA1 production in breast and/or ovarian cancer cells. Such a method can include: providing a compound as described herein (e.g., compounds 1-38 and/or Formulas A-I); and administering a therapeutically effective amount of the compound to a subject so as to increase BRCA1 production. The increased BRCA1 production can be sufficient to inhibit the growth and/or propagation of breast and/or ovarian cancer cells. The increased BRCA1 production can be increased compared to BRCA1 production in the subject prior to being administered the compound.

In one embodiment, the present invention can include a cancerous breast or ovarian cell comprising a therapeutically effective amount of a compound having a structure as described herein (e.g., compounds 1-38 and/or Formulas A-I) so as to induce or increase BRCA1 production in the cell. The BRCA1 production can be increased from a low level of the BRCA1 production in the cell.

These and other embodiments and features of the present invention will become more fully apparent from the following description and appended claims, or may be learned by the practice of the invention as set forth hereinafter.

FIGURES

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 1 includes a graph illustrating luciferase activity in MCF7 cells transfected with pGL4.14-hBRCA1 (pGL4.14 luciferase reporter plasmid containing the human BRCA1 promoter).

Figure 2:
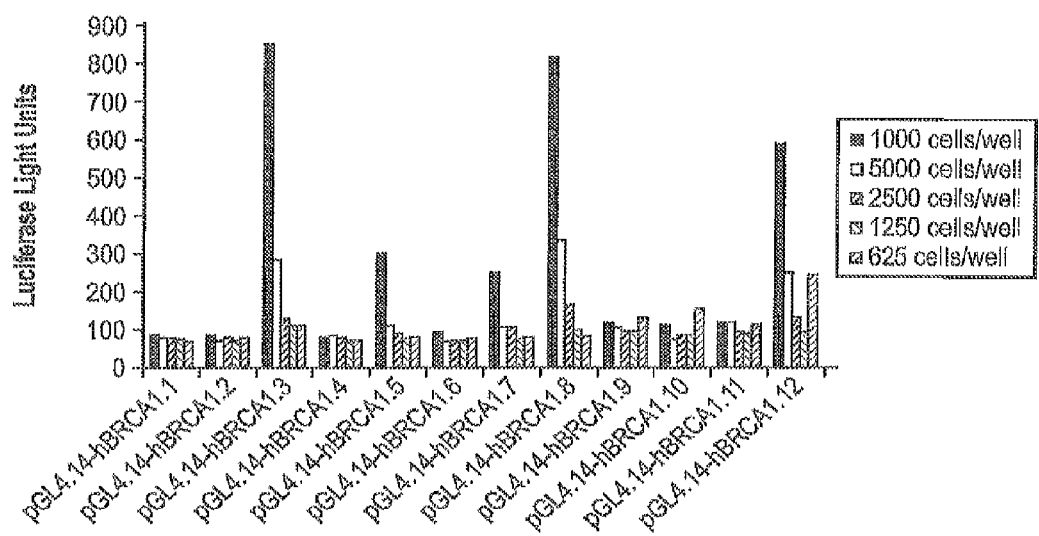

FIG. 2 includes a graph illustrating luciferase activity in MCF7 cells transfected with subclones of pGL4.14-hBRCA-1.

Figure 3A:
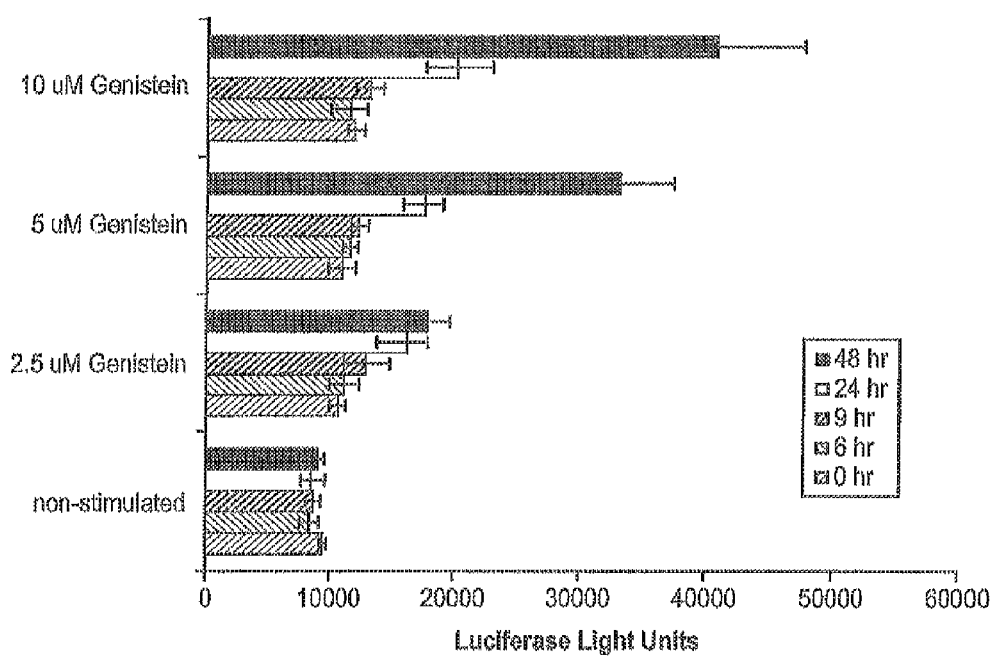

FIG. 3A includes a graph illustrating luciferase activity in MCF7 cells transfected with pGL4.14-hBRCA1.3 that were treated with the indicated concentration of genistein for 0, 6, 9, 24 and 48 hours.

Figure 3B:
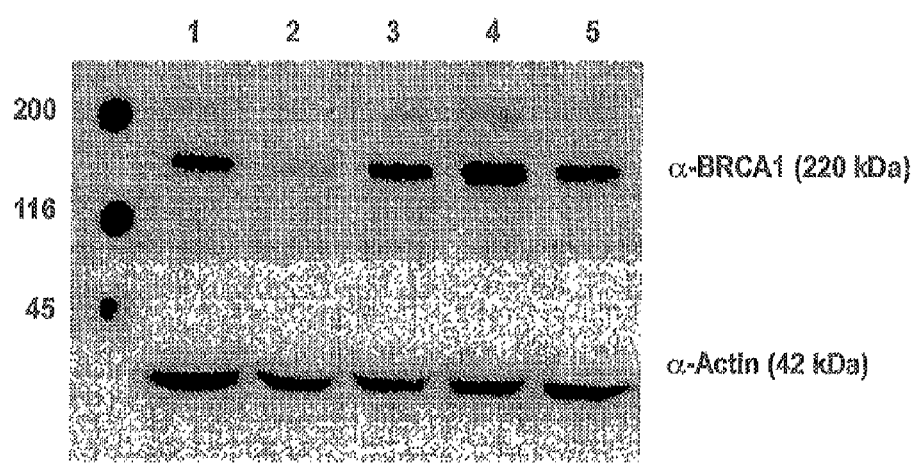

FIG. 3B includes a picture of a Western Blot illustrating the increase in BRCA1 protein in MCF7 cells that were either left nonstimulated (lane 1), treated with DMSO (lane 2) or 1, 10 and 30 µM of genistein (lanes 3-5, respectively) for 48 hours.

Figure 4A:
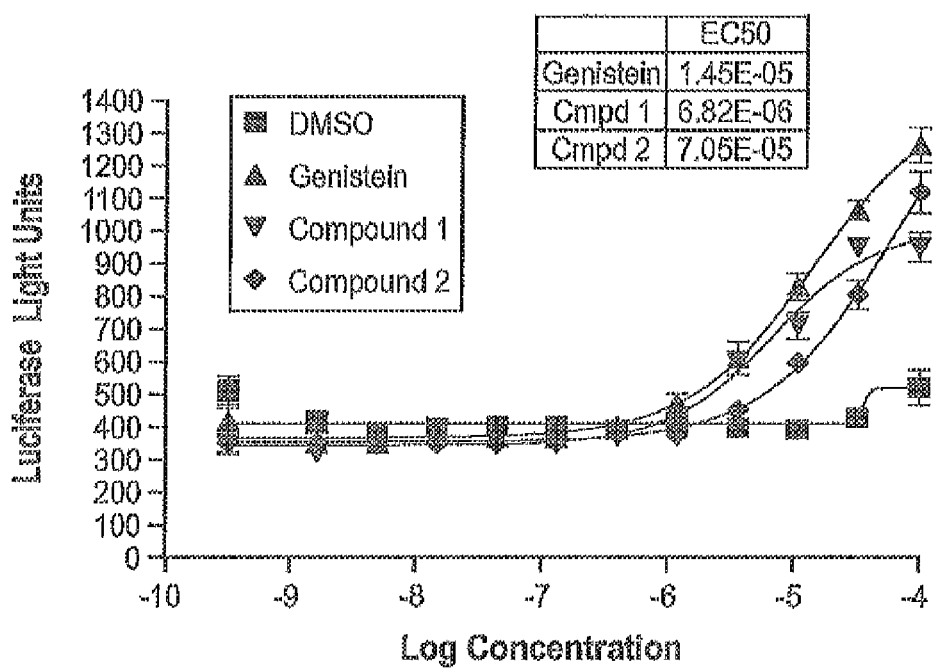

FIG. 4A includes a graph illustrating luciferase activity in MCF7 cells transfected with pGL4.14-hBRCA1.3 that were treated with compounds of the present invention, wherein luciferase activity is proportional to increase in BRCA1.

Figure 4B:
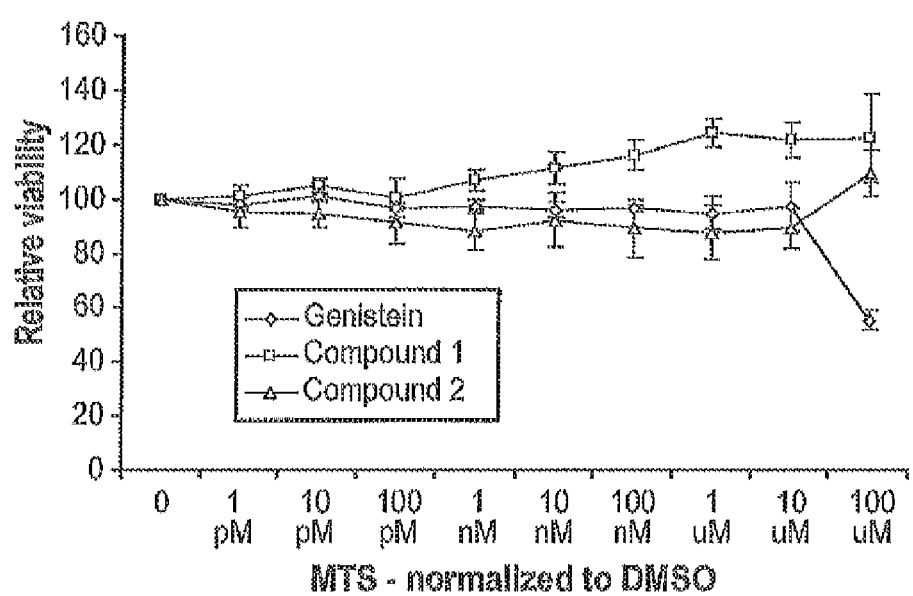

FIG. 4B includes a graph illustrating cell viability of MCF7 cells transfected with pGL4.14-hBRCA 1.3 that were treated with compounds of the present invention.

Figure 5A:
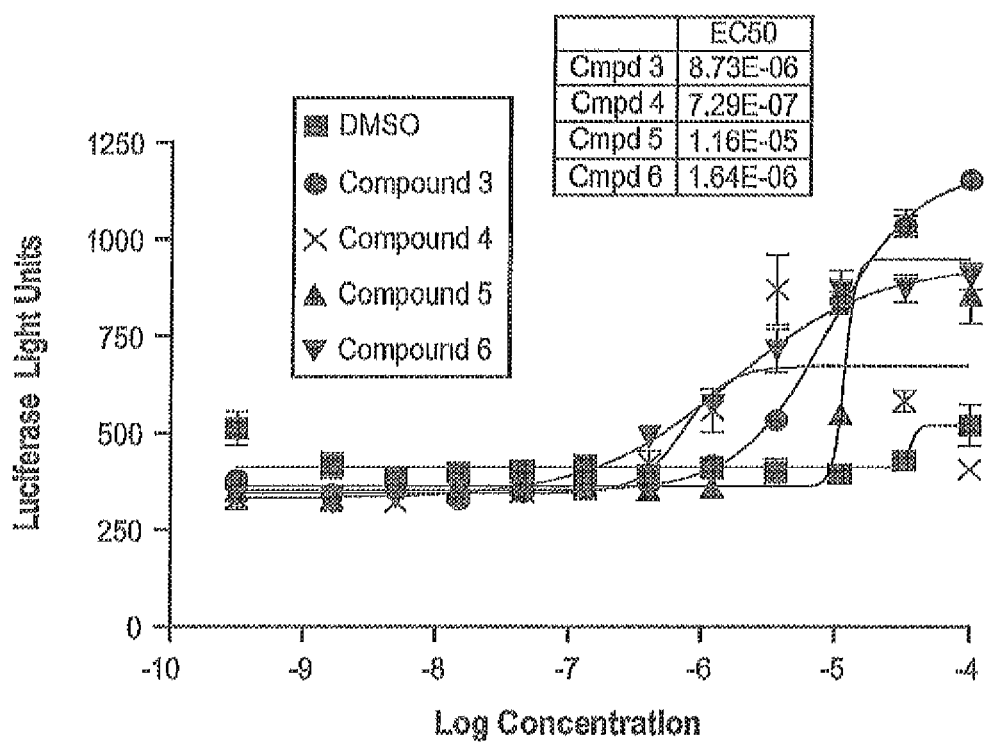

FIG. 5A includes a graph illustrating luciferase activity in MCF7 cells transfected with pGL4.14-hBRCA1.3 that were treated with compounds of the present invention, wherein luciferase activity is proportional to increase in BRCA1.

Figure 5B:
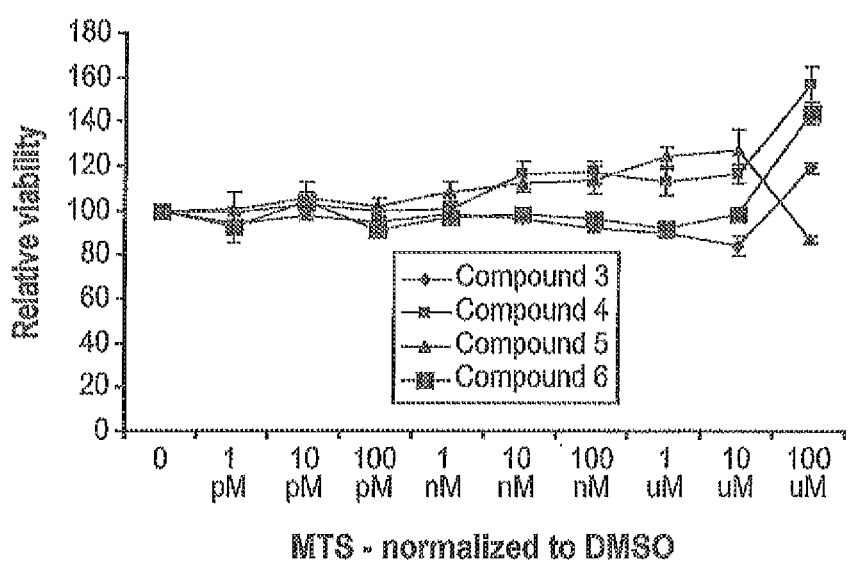

FIG. 5B includes a graph illustrating cell viability of MCF-7 cells transfected with pGL4.14-hBRCA1.3 that were treated with compounds of the present invention.

Figure 6A:
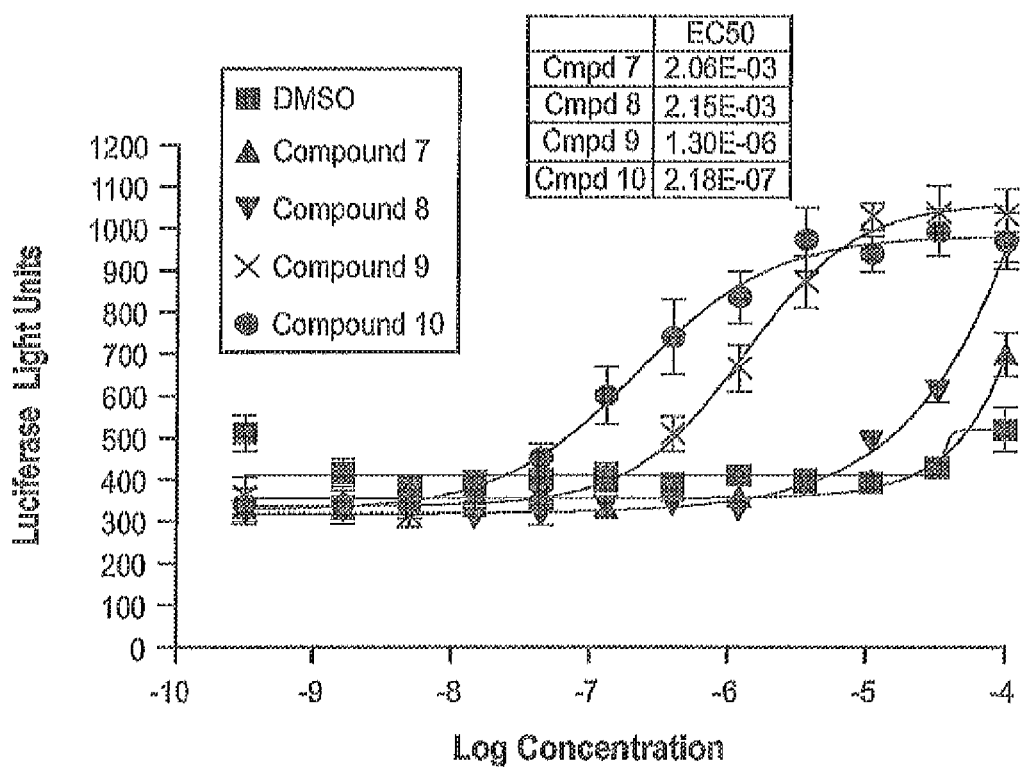

FIG. 6A includes a graph illustrating luciferase activity in MCF7 cells transfected with pGL4.14-hBRCA1.3 that were treated with compounds of the present invention, wherein luciferase activity is proportional to increase in BRCA1.

Figure 6B:
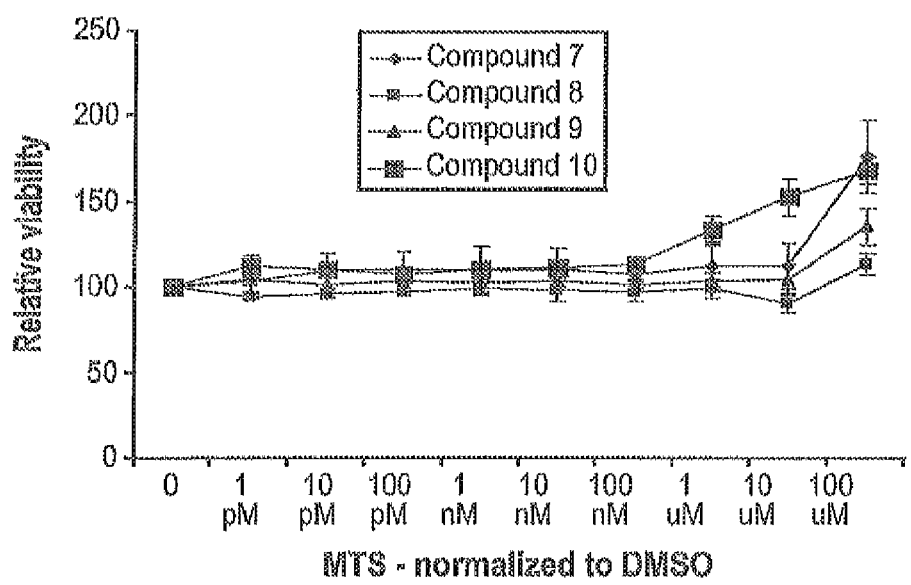

FIG. 6B includes a graph illustrating cell viability of MCF7 cells transfected with pGL4.14-hBRCA1.3 that were treated with compounds of the present invention.

Figure 7A:
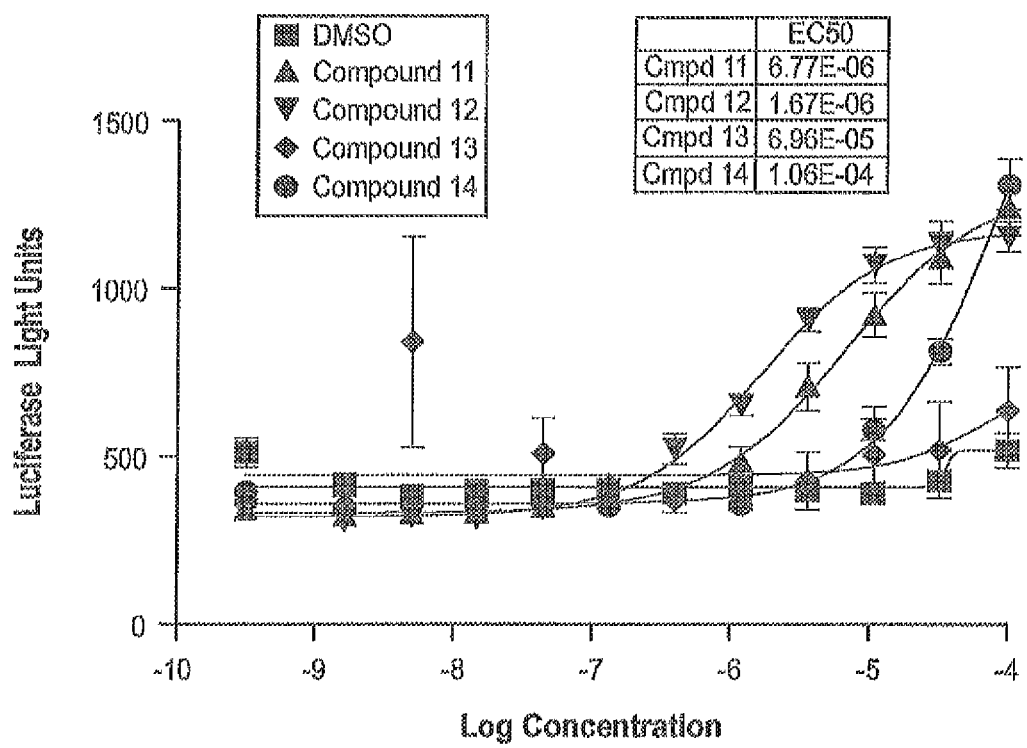

FIG. 7A includes a graph illustrating luciferase activity in MCF7 cells transfected with pGL4.14-hBRCA1.3 that were treated with compounds of the present invention, wherein luciferase activity is proportional to increase in BRCA1.

Figure 7B:
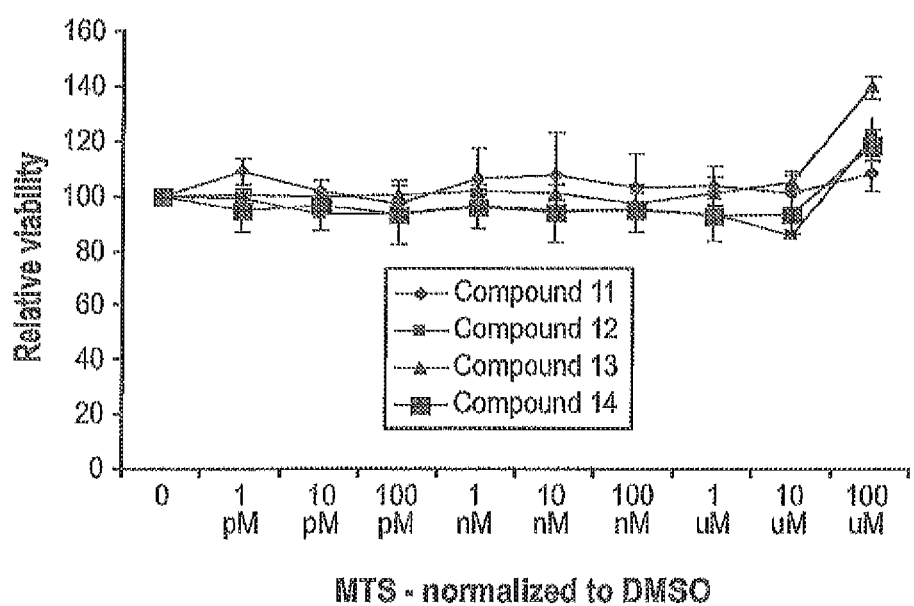

FIG. 7B includes a graph illustrating cell viability of MCF7 cells transfected with pGL4.14-hBRCA 1.3 that were treated with compounds of the present invention.

Figure 8A:
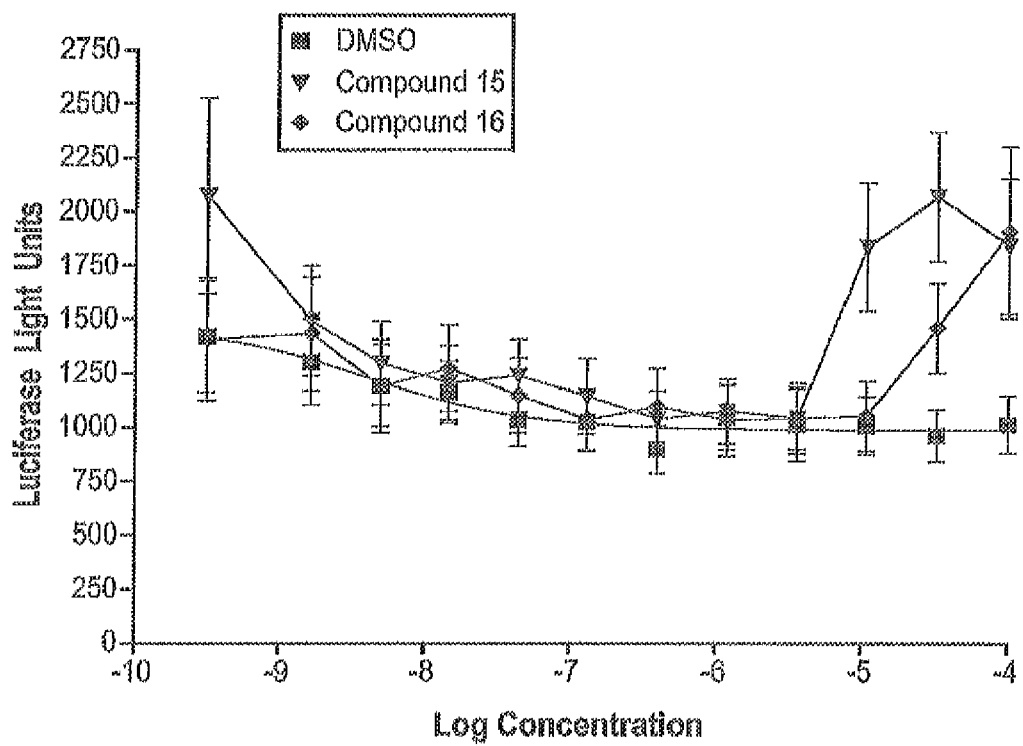

FIG. 8A includes a graph illustrating luciferase activity in MCF7 cells transfected with pGL4.14-hBRCA1.3 that were treated with compounds of the present invention, wherein luciferase activity is proportional to increase in BRCA1.

Figure 8B:
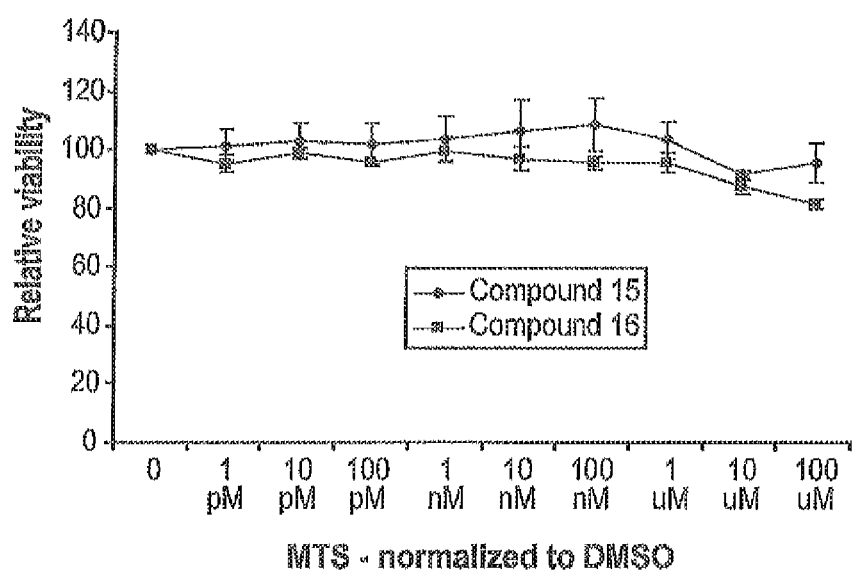

FIG. 8B includes a graph illustrating cell viability of MCF7 cells transfected with pGL4.14-hBRCA1.3 that were treated with compounds of the present invention.

Figure 9A:
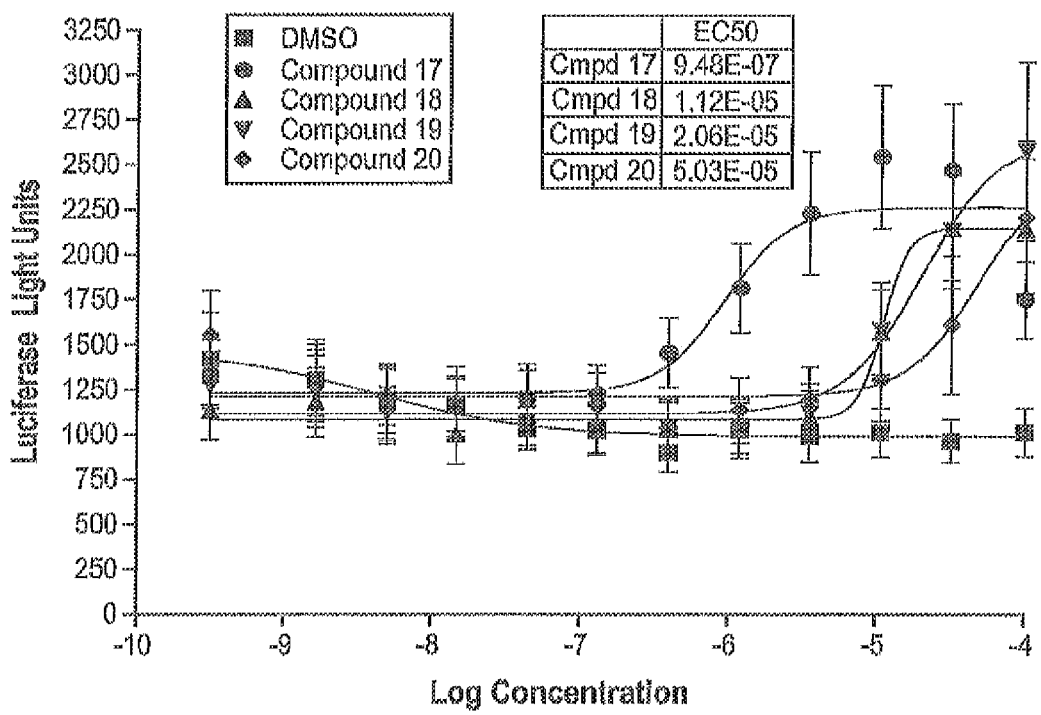

FIG. 9A includes a graph illustrating luciferase activity in MCF7 cells transfected with pGL4.14-hBRCA1.3 that were treated with compounds of the present invention, wherein luciferase activity is proportional to increase in BRCA1.

Figure 9B:
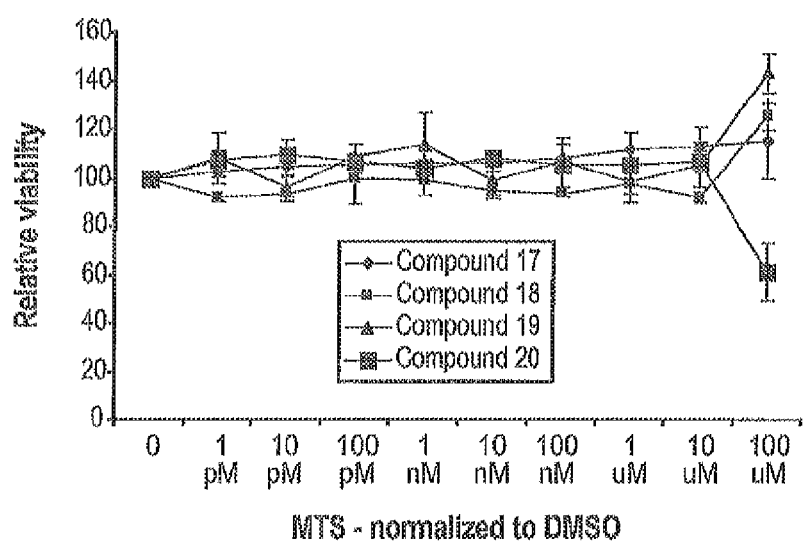

FIG. 9B includes a graph illustrating cell viability of MCF7 cells transfected with pGL4.14-hBRCA1.3 that were treated with compounds of the present invention.

Figure 10A:
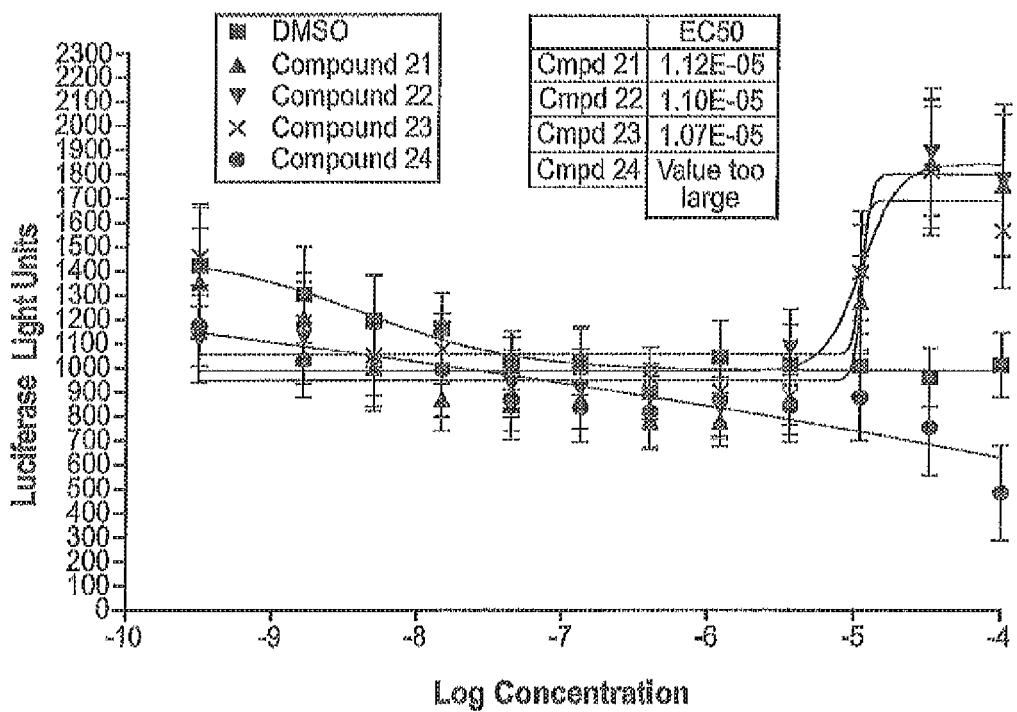

FIG. 10A includes a graph illustrating luciferase activity in MCF7 cells transfected with pGL4.14-hBRCA1.3 that were treated with compounds of the present invention, wherein luciferase activity is proportional to increase in BRCA1.

Figure 10B:
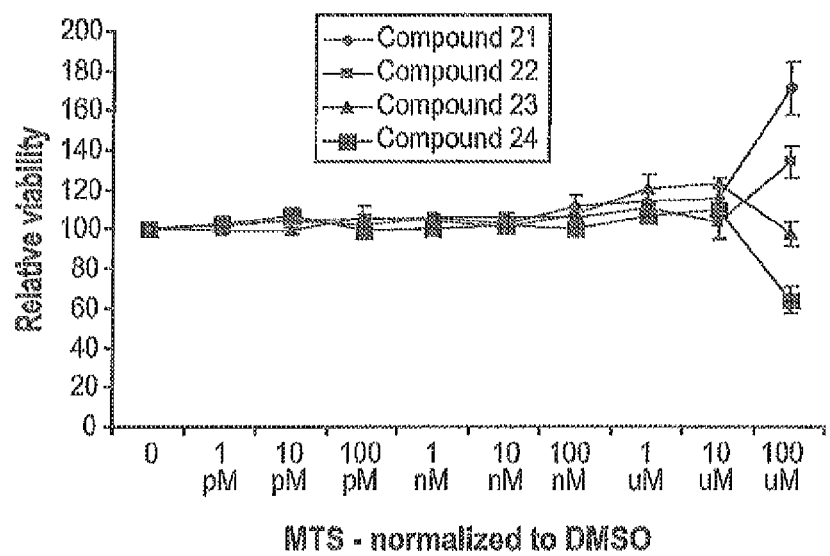

FIG. 10B includes a graph illustrating cell viability of MCF7 cells transfected with pGL4.14-hBRCA1.3 that were treated with compounds of the present invention.

Figure 11A:
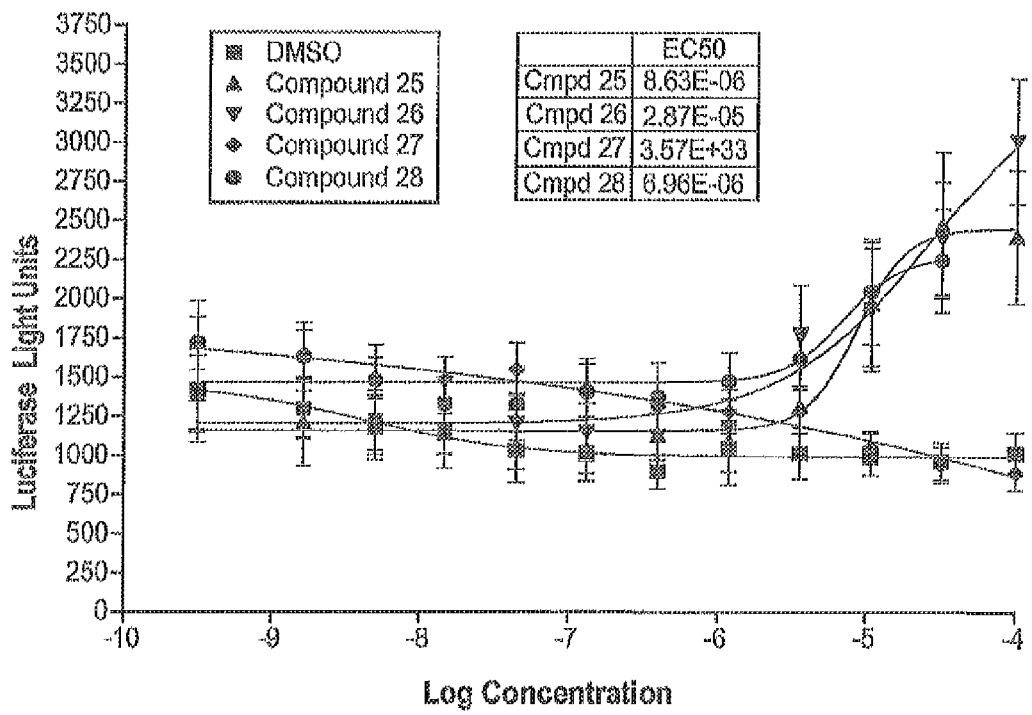

FIG. 11A includes a graph illustrating luciferase activity in MCF7 cells transfected with pGL4.14-hBRCA1.3 that were treated with compounds of the present invention, wherein luciferase activity is proportional to increase in BRCA1.

Figure 11B:
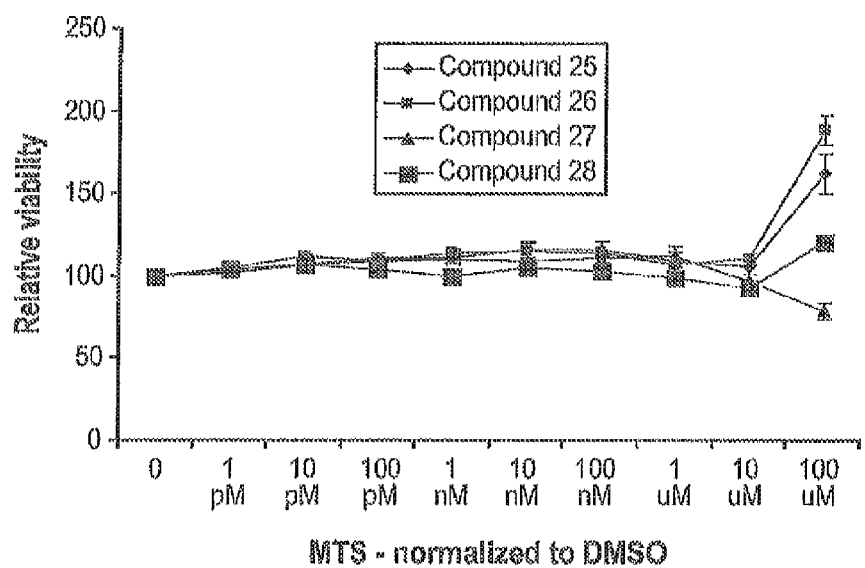

FIG. 11B includes a graph illustrating cell viability of MCF7 cells transfected with pGL4.14-hBRCA1.3 that were treated with compounds of the present invention.

Figure 12:
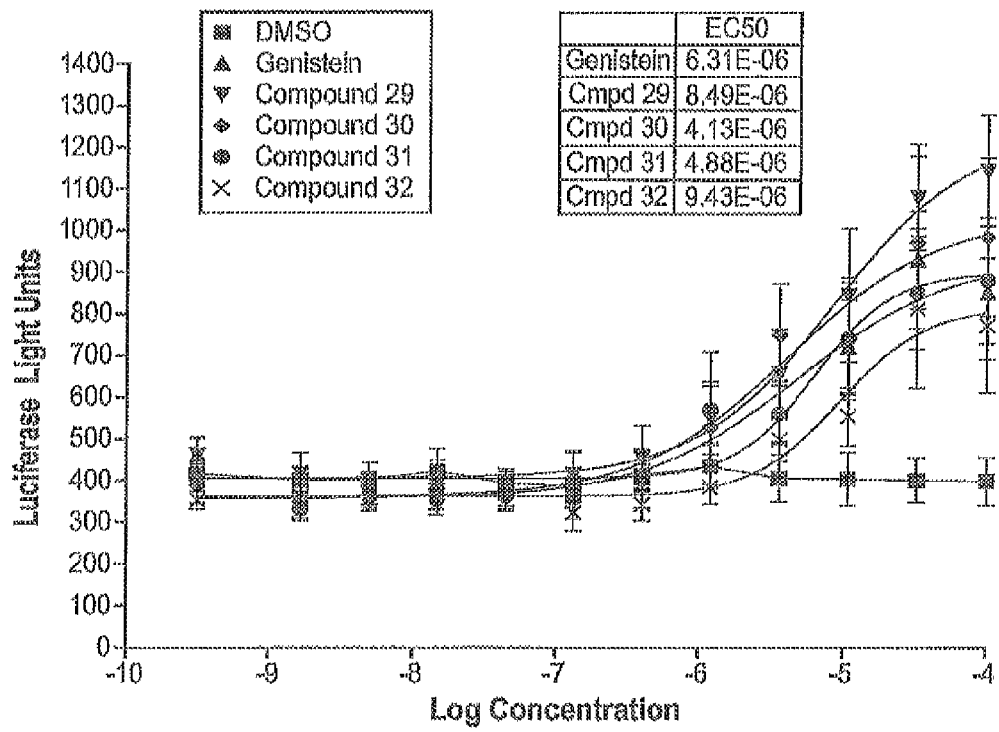

FIG. 12 includes a graph illustrating luciferase activity in MCF7 cells transfected with pGL4.14-hBRCA1.3 that were treated with compounds of the present invention, wherein luciferase activity is proportional to increase in BRCA1.

Figure 13:
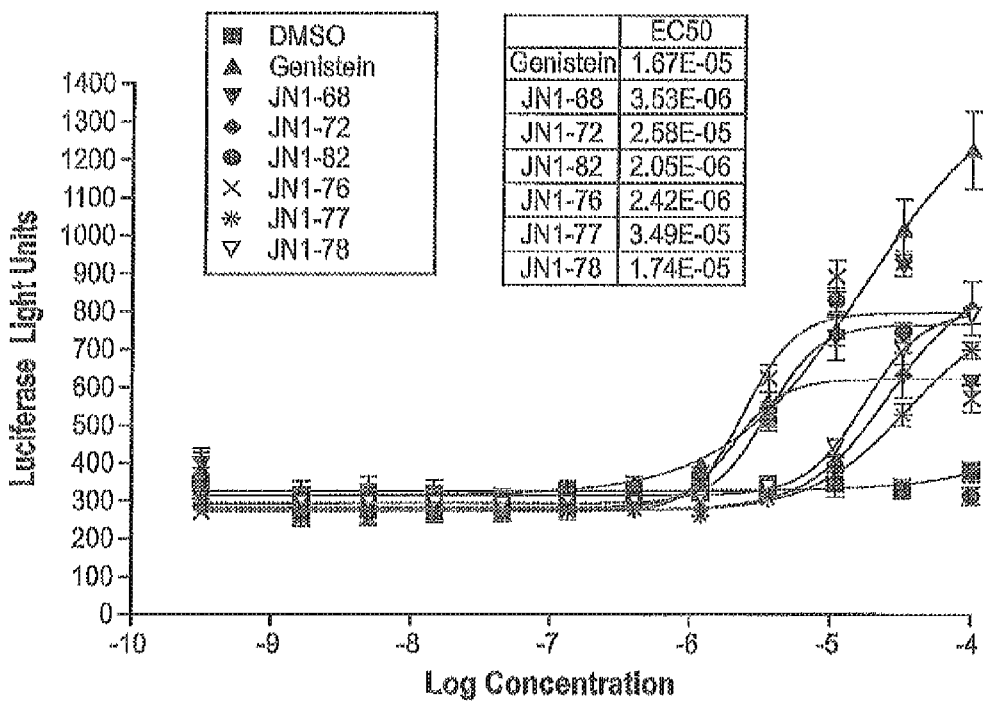

FIG. 13 includes a graph illustrating luciferase activity in MCF7 cells transfected with pGL4.14-bBRCA1.3 that were treated with compounds of the present invention, wherein luciferase activity is proportional to increase in BRCA1.

Figure 14A:
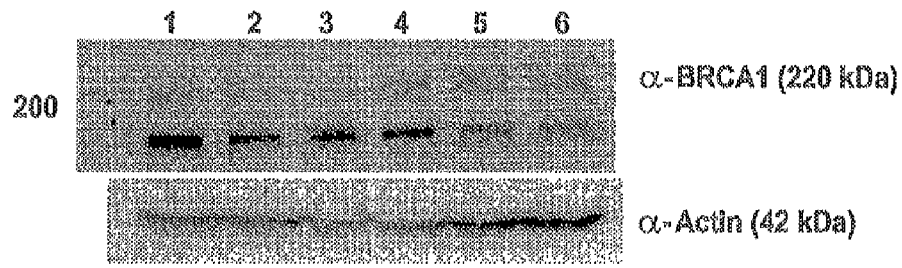

FIG. 14A includes a picture of a Western Blot illustrating the increase in BRCA1 protein in MCF-7 cells transfected with pGL4.14-hBRCA1.3 that were treated with compound 29 of the present invention.

Figure 14B:
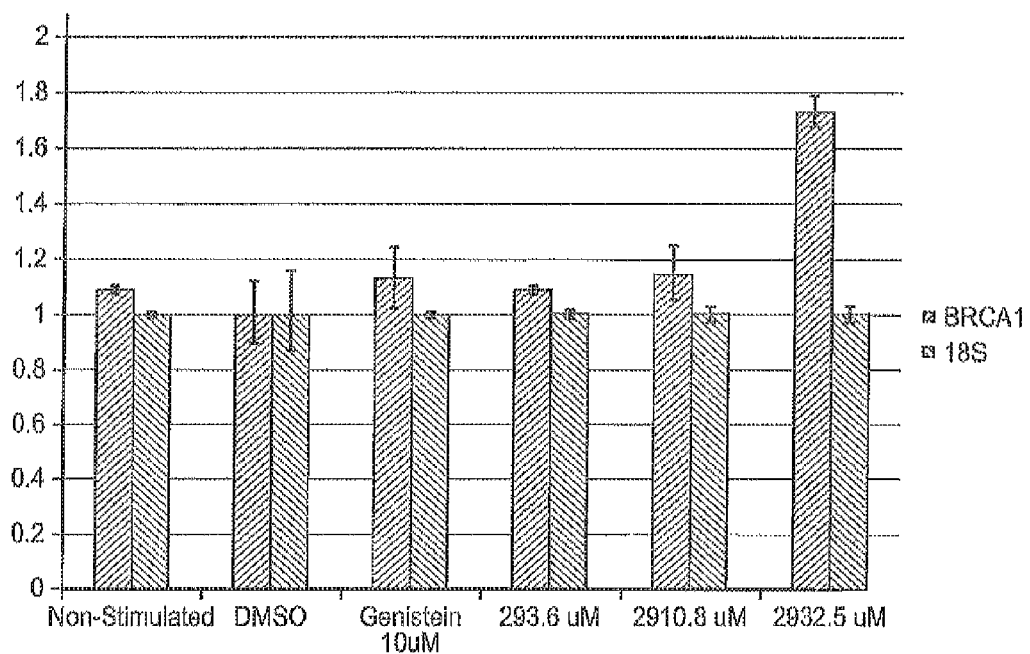

FIG. 14B includes a graph illustrating amount of BRCA1 and 18S RNA production in MCF-7 cells transfected with pGL4.14-hBRCA1.3 that were treated with compound 29 of the present invention.

Figure 15A:
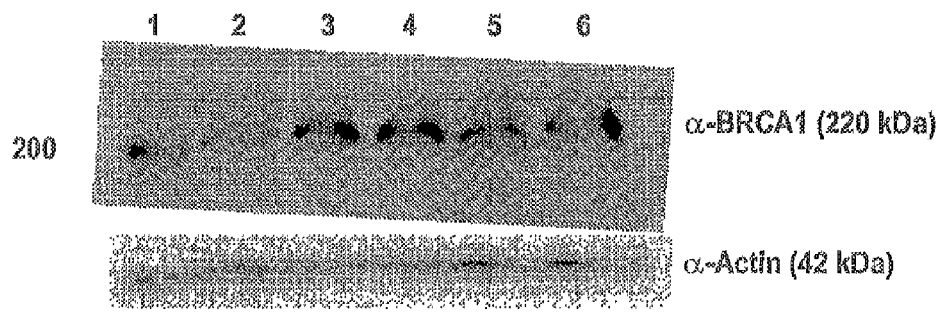

FIG. 15A includes a picture of a Western Blot illustrating the increase in BRCA1 in MCF-7 cells transfected with pGL4.14-hBRCA1.3 that were treated with compound 30 of the present invention.

Figure 15B:
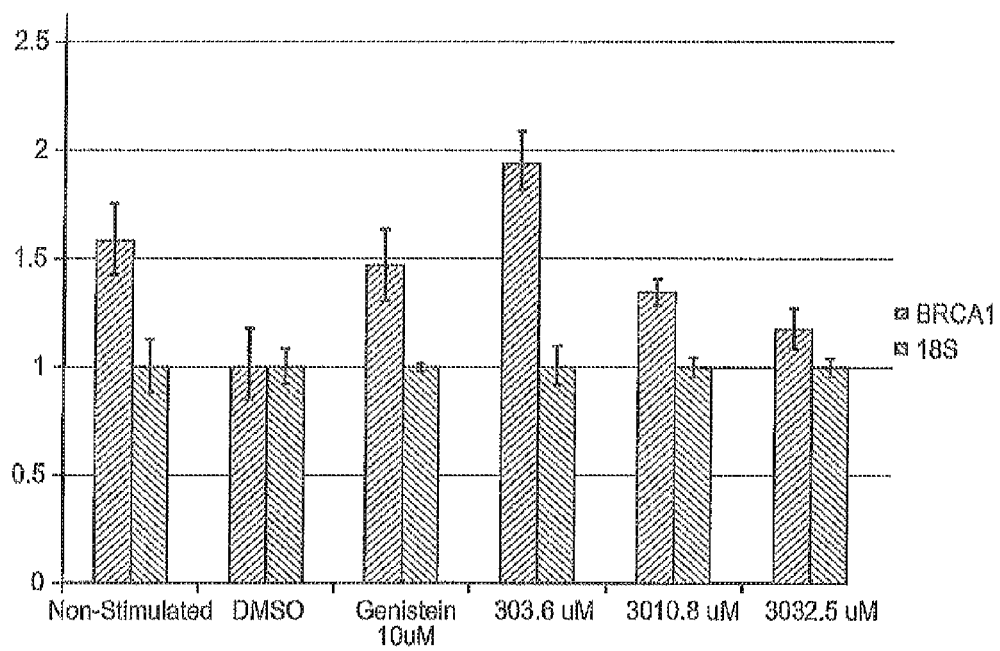

FIG. 15B includes a graph illustrating amount of BRCA1 and 18S RNA production in MCF-7 cells transfected with pGL4.14-hBRCA1.3 that were treated with compound 30 of the present invention.

Figure 16:
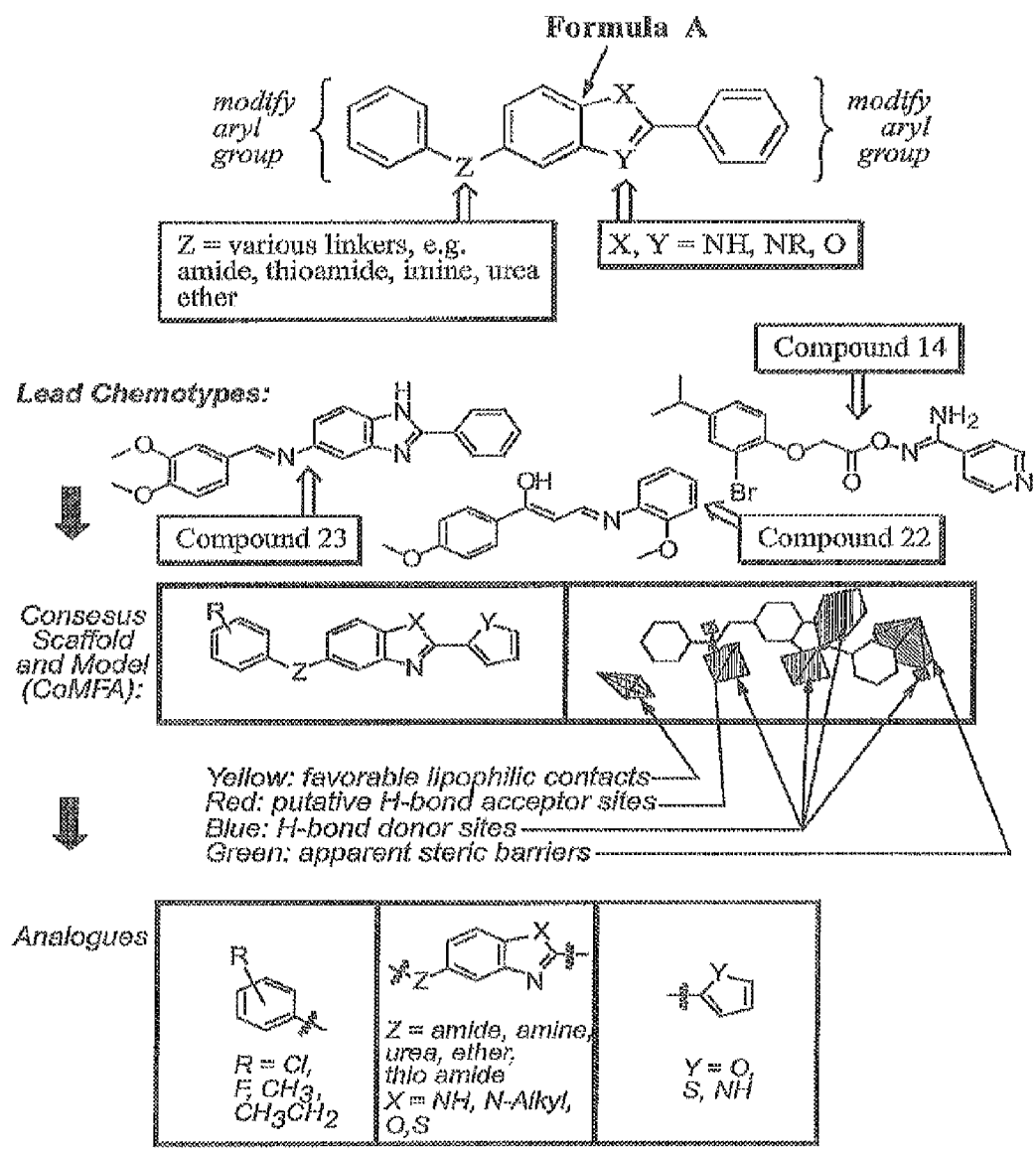
Figure 17A:
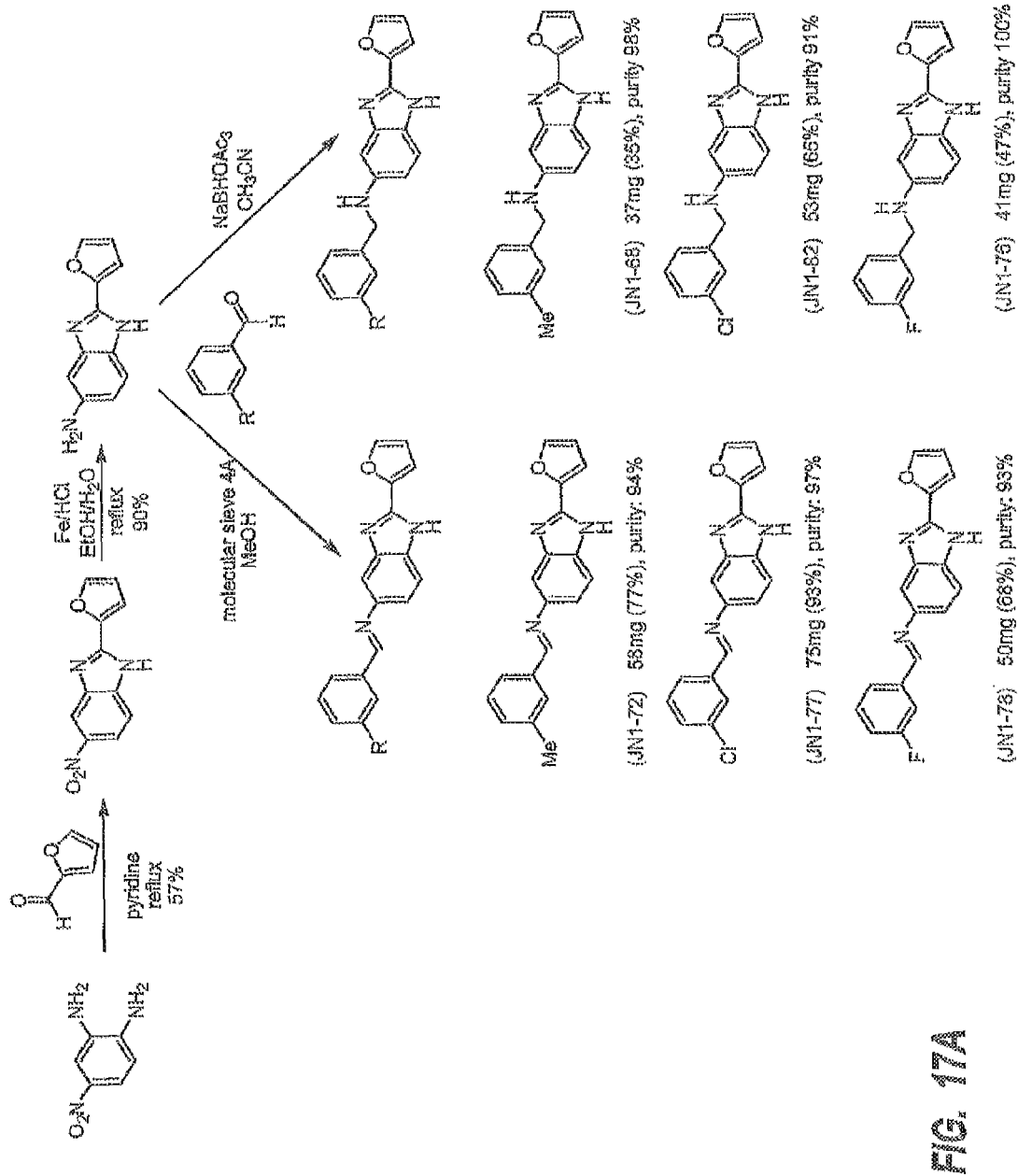
Figure 47B:
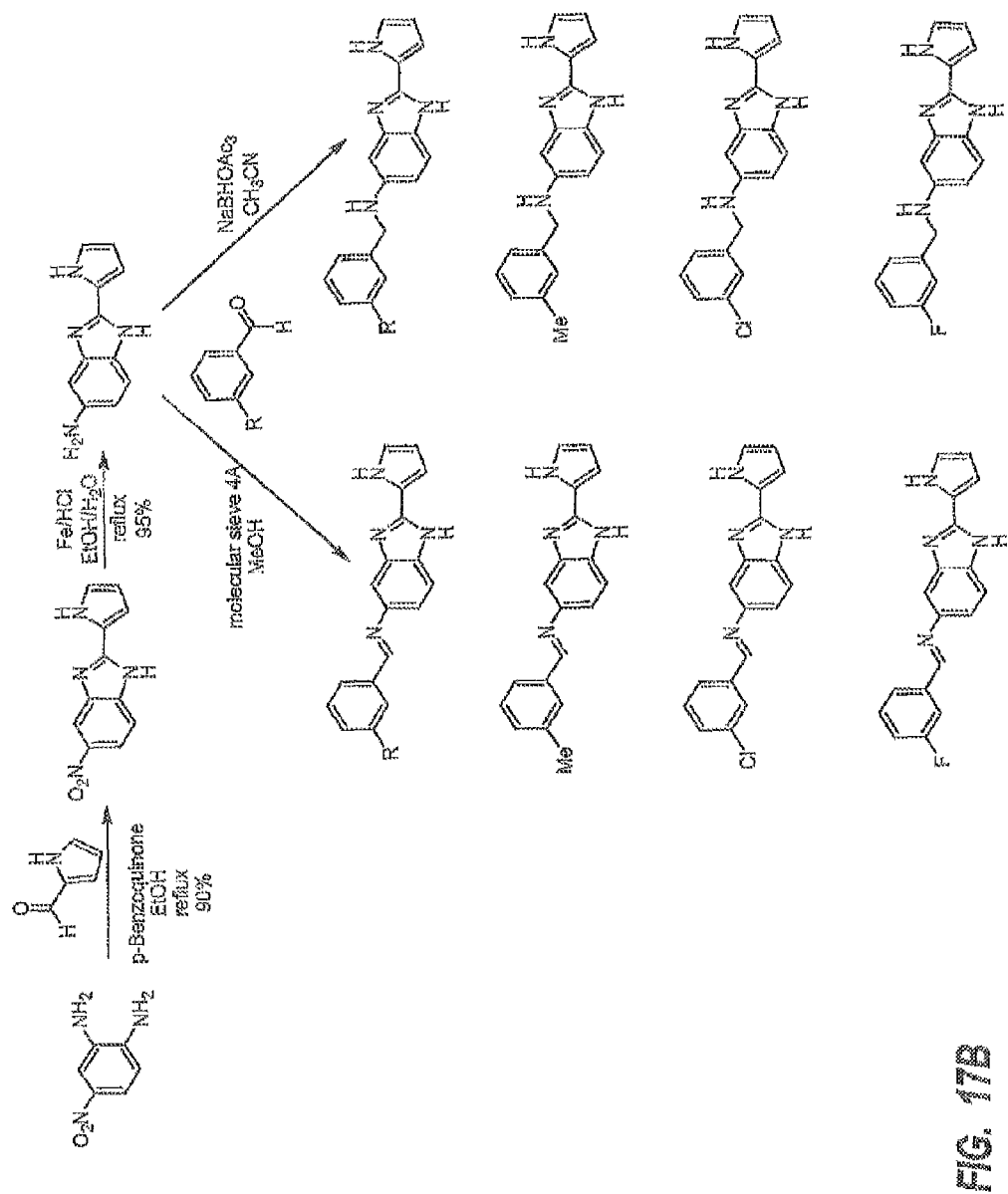
Figure 17C:
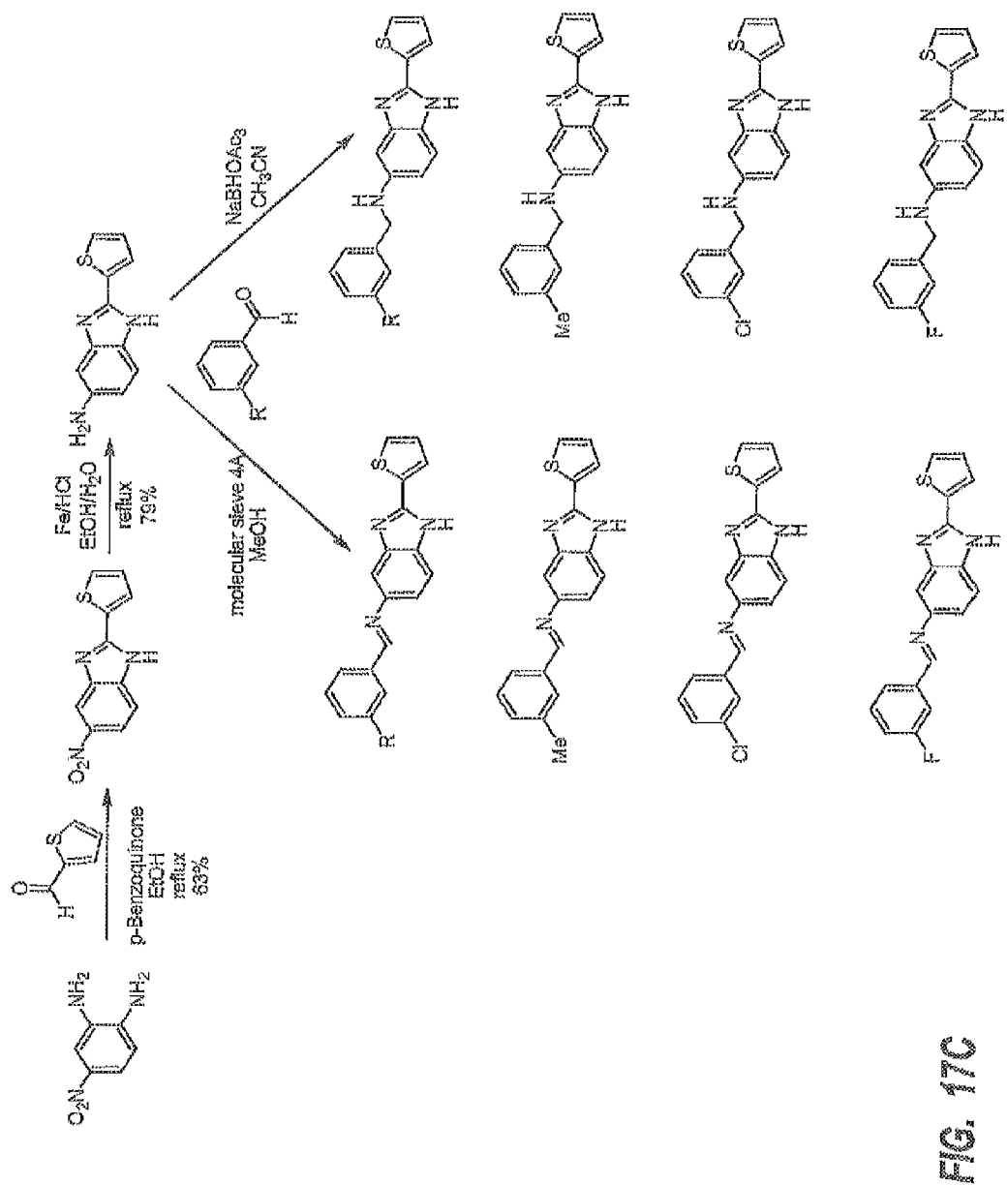
Figure 17D:
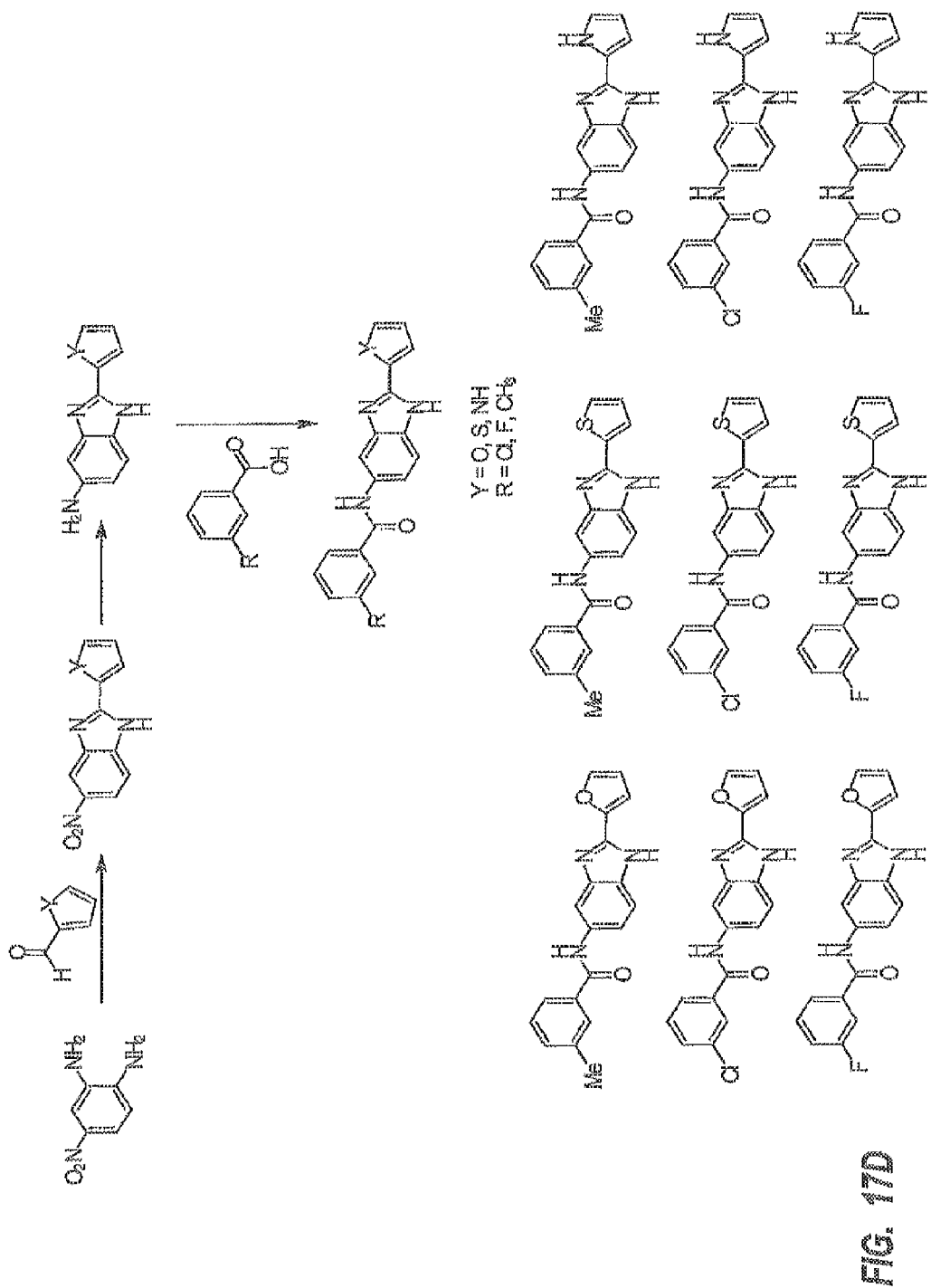

FIG. 16 includes an illustration of a process for selecting analogs of compounds that increase BRCA1 in accordance with the present invention.

FIGS. 17A-17D include illustrations of chemical synthesis processes for preparing analogs of compounds that increase BRCA1 in accordance with the present invention.

DETAILED DESCRIPTION

The compounds of the present invention have been identified by drug screening with the human BRCA1 promoter as the target. A unique feature of the present invention is the use of these compounds to increase BRCA1 production, and to delay or inhibit breast and/or ovarian tumor growth. Other tumor suppressors are drug targets, but do not enhance the production of BRCA1. Increasing production of BRCA1 is advantageous because BRCA1 is not mutated in 90% of breast and ovarian cancers; rather it is simply turned off. Thus, increasing production of BRCA1 can prevent and/or treat breast and ovarian cancer.

I. Introduction

The BRCA1 gene is composed of 24 exons and the encoded protein is 1863 amino acid residues with an apparent molecular mass of 220 kDa. The regulatory region of the human BRCA1 gene has two TATA-less promoters ($\alpha$ and $\beta$) and both positive and negative regulatory factors have been identified to regulate BRCA1 expression.

BRCA1 is responsive to the systemic hormones estrogen, progesterone, and prolactin. Additionally, the phytochemicals, indole-3-carbinol, genistein, and daidzein increase BRCA1 mRNA and reduce mammary tumorigenesis. Although the regulatory mechanisms responsible for BRCA1 transcriptional regulation are not fully understood, it is clear that modulation of the BRCA1 promoter directly effects BRCA1 expression. Functionally, BRCA1 has been implicated in a wide array of cellular activities including DNA damage repair, cell-cycle checkpoint control, growth inhibition, apoptosis, transcriptional regulation, chromatin remodeling, and protein ubiquitylation. Recently, BRCA1 has been demonstrated to have a role in mammary stem cell self-renewal and differentiation. These studies demonstrated that loss of BRCA1 leads to an expansion of the cancer stem cell niche ($CD44^+/CD24^-$/low, CD133), whereas expression of BRCA1 leads to differentiation of the breast epithelium and no tumor development.

BRCA1 has been intensely investigated and mutations in the BRCA1 gene have been found to account for half of the hereditary breast cancer cases and almost all hereditary breast and ovarian cancer cases. Although the role of BRCA1 in sporadic breast and ovarian cancer is still uncertain, decreased BRCA1 expression often accompanies sporadic breast cancer progression. Restoration of functional BRCA1 protein levels to breast epithelial cells provides protection against the development of mammary gland neoplasia. Additionally, overexpression of BRCA1 in the murine mammary gland provides protection against mutagen-induced mammary neoplasia. Thus, drug candidates that increase expression and/or function of BRCA1 may prove to treat, inhibit, or prevent cancer, such as breast or ovarian cancer.

In order to study whether or not a drug candidate can increase expression and/or function of BRCA1, the human breast cancer cell line, MCF7, was stably transfected with the human BRCA1 promoter-driven luciferase reporter plasmid. This cell line was used to establish a screening assay to identify drug compounds that elevate BRCA1 expression levels, using luciferase activity as the end-point readout. As such, an assay can be performed to test for increased luciferase activity, which is directly proportional to increased BRCA1. After experimental parameters were established, over 100,000 small molecules were screened for their ability to increase BRCA1-luciferase levels. A number of plausible active compounds were identified and structure activity relationship models were developed.

Compounds have been biologically and chemically characterized for their ability to activate the BRCA1 promoter. Increased expression of functional BRCA1 protein levels in breast epithelial cells can provide protection against the development of mammary gland neoplasia in women with wild-type BRCA1 alleles, and thereby may treat, inhibit, and/or prevent cancer related to BRCA1.

In vitro validation screens can be conducted on compounds identified in the primary drug screen (e.g., increased luciferase). Lead compounds can be tested for their ability to augment endogenous BRCA1 protein and mRNA levels. Compounds that are verified in the in vitro screen so as to increase endogenous BRCA1 protein and mRNA levels can be further characterized for their effects on BRCA1 functions, such as DNA repair. The specificity of the identified compounds can be tested for the effective concentration ($EC_{50}$), and characterized for the effects on endogenous BRCA1 expression and function.

A compound that, at the lowest concentration, can result in the greatest increase in BRCA1 expression is desirable. The compound may be involved in a direct mechanism for modulation of BRCA1 expression, such as: modulation of DNA binding proteins; modulation of the half-life of the messenger RNA; or modulation of post-transcriptional modifications. It is beneficial for the compound to be specific for increasing BRCA1 so that there is a minimum modulation of other genes to decrease potential side effects. Microarray studies can be conducted to identify the degree of specificity of the compounds for BRCA1. Additionally, it may be advantageous for a compound to not increase the expression of genes involved in proliferation or cell cycle progression, and effects on BRCA1 function in the previously mentioned pathways, other functions can be evaluated, including transcriptional regulation, chromatin remodeling, substrate ubiquitylation, and stem cell regulation.

Compounds that are active for increasing BRCA1 can be analyzed with structure-activity relationship (SAR) models to characterize physical-chemical properties that are related to the function of increasing BRCA1. In silico studies using the program VolSurf can be used to predict ADME properties and refine structure-activity relationship models. Analogues of active compounds can be synthesized to further enhance activity of a lead compound. In vitro and in vivo studies can be conducted to characterize the pharmacology, drug safety, and pharmacokinetics of compounds and analogs that increase BRCA1.

The pharmacological properties of compounds that increase BRCA1 can also be studied, such as the rationally designed analogues, or libraries of analogs. The compounds can be studied to identify compounds with optimized affinity, specificity, solubility, and bioavailability through SAR studies, including directed library design and synthesis, use of computational tools, and structure-based drug design. Also, compounds can be identified as drug candidates based on their "drugability" properties. An ideal, optimized "drugability" compound can have single digit nanomolar potency, >100-fold selectivity, and >10 μg/ml solubility.

Previous studies have demonstrated an overexpression of human BRCA1 can delay the onset of 7,12-dimethylbenz[alpha]anthracene (DMBA)-induced tumorigenesis in the murine mammary gland, and the compounds of the present invention can be screened against DMBA-induced tumorigenesis to identify an optimum drug candidate. The drug candidate can be tested for the activity of increasing Brca1 expression in vivo and the potential of a candidate drug to delay onset of mammary tumors via Brca1 upregulation will also be tested. Mice dosed with a candidate drug will be treated with DMBA to induce mammary tumorigenesis and time to palpable tumor formation will be determined. In order to test therapeutic efficacy DMBA would be administered first, tumors would be allowed to develop, and then candidate drug dosage would be administered. Tumor growth kinetics would be followed to determine therapeutic effect.

The chemical compounds identified in the drug screening assay increased the production of BRCA1 in tumor cell lines, which indicates that the chemical compounds can be beneficial for increasing production of BRCA1 in breast and/or ovarian tumor cells. BRCA1 has also been implicated in prostate and pancreatic cancer, so the compounds may also have an affect on these cancers. Thus, the compounds identified in the drug discovery project (e.g., screening for enhanced production of BRCA1) can be used to treat, inhibit, or prevent breast and ovarian cancer, but may also be used in other tumors, such as prostate and pancreatic tumors.

II. Screening

The human BRCA1 promoter was cloned and inserted upstream of a luciferase firefly reporter gene. The BRCA1-luciferase reporter vector was then used to transfect the breast cancer cell line, MCF7. Hygromycin was used to select for those MCF7 cells that contained the vector. MCF7 cells containing the vector were screened against different chemical libraries, and chemicals showing an increase in luciferase activity were identified as increasing the level of human BRCA1 promoter activity, and thereby being capable of increasing BRCA1 production. Increased luciferase activity was utilized as an indicator for a compound having increased BRCA1 promoter activity.

The compounds that increased BRCA1-luciferase activity were screened again at varying concentrations. Such additional screening at various concentrations verified the original screening data, and additionally provided a concentration that resulted in maximal BRCA1-luciferase activity. The compounds were also examined for toxicity to the MCF7 cells. Additionally, the compounds can be examined for their ability to increase endogenous BRCA1 protein expression by western blotting. Western blotting methods test the compounds for their ability to increase BRCA1 protein expression. Quantitative Real-Time Polymerase chain reaction (qRT-PCR) can also be used to identify BRCA1 RNA production increases.

Identification of a compound that increases BRCA1 protein expression can be used in developing a successful therapy in preventing and/or treating breast and/or ovarian cancer. If a compound does not increase BRCA1 protein expression sufficiently but shows potential, the compound can be derivatized and analogued by medicinal chemists and tested again. The compounds that increase BRCA1 protein expression can be utilized in the methods of treating, inhibiting, and/or preventing and/or treating breast and/or ovarian cancer.

The compounds that increase BRCA1 protein expression can be evaluated by medicinal chemists and derivatives and analogues can be generated. The derivatives/analogues can be similarly tested for their ability to increase BRCA1 expression in vitro and then in vivo.

All of the compounds that have BRCA1 activity (e.g., increased expression) can be tested for absorption, distribution, metabolism and excretion properties. Those compounds with ideal pharmacokinetics and BRCA1 expression can then be tested in mouse models (e.g., in vivo) for their ability to increase Brca1 in the mouse and prevent the onset of mammary tumors following exposure to a carcinogen, such as DMBA.

The compounds described herein (e.g., Compounds 1-38, shown below) can increase BRCA1 expression. As such, these compounds can be used in treating, inhibiting, and/or preventing breast and/or ovarian cancer. Thus, pharmaceutical compositions comprising the compounds described herein can be prepared for being administered to a subject to treat, inhibit, and/or prevent breast and/or ovarian cancer, as well as other cancers.

As shown herein, the compounds of the present invention can be represented by Compounds 1-38, as shown below. It is thought that at least some of the chemical compounds of Compounds 1-38 may increase BRCA1 expression by enhancing the BRCA1 promoter function. This is shown by the increase in luciferase activity in the BRCA1-luciferase system.

III. Analogs/Derivatives

The small molecules of Formulas I-32 that were found to increase BRCA1 are candidates for derivatization. As such, Compounds 1-32 can be prepared into analogues that have modulated potency, selectivity, and solubility in order to provide useful leads for drug discovery and drug development. During optimization, new analogues can be designed considering issues of drug delivery, metabolism, novelty, and safety. The information obtained from Compounds 1-32 was used in order to design compounds 33-38.

Additionally, any of the compounds of Compounds 1-38 can be derivatized/analogued as is well known in the art of combinatorial and medicinal chemistry. The analogs or derivatives can be prepared by adding and/or substituting functional groups at various locations on any of compounds of Compounds 1-38. As such, the compounds of Compounds 1-38 can be converted into derivatives/analogues using well known chemical synthesis procedures. For example, all of the hydrogen atoms or substituents can be selectively modified to generate new analogues. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog", "analogue," or "derivative" is meant to refer to a chemical compound or molecule made from a parent compound or molecule by one or more chemical reactions. As such, an analog can be a compound with a structure similar to that of Compounds 1-32 (or 1-38) or based on a scaffold of Compounds 1-32 (or 1-38), but differing from it in respect to certain components or structural makeup, which may have a similar or opposite action metabolically. An analog or derivative of any of Compounds 1-32 (or 1-38) in accordance with the present invention can be used to prevent and/or treat breast and/or ovarian cancer.

In one embodiment, the compounds of Compounds 1-38 can independently be derivatized/analogued by modifying hydrogen groups independently from each other into other substituents. That is, each atom on each molecule can be independently modified with respect to the other atoms on the same molecule. Any traditional modification for producing a derivative/analogue can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

In one embodiment, the compounds can be described by the chemical structures of Formulas A-I.

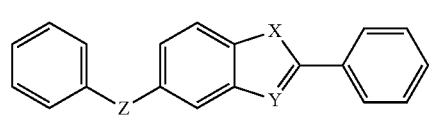

Formula A

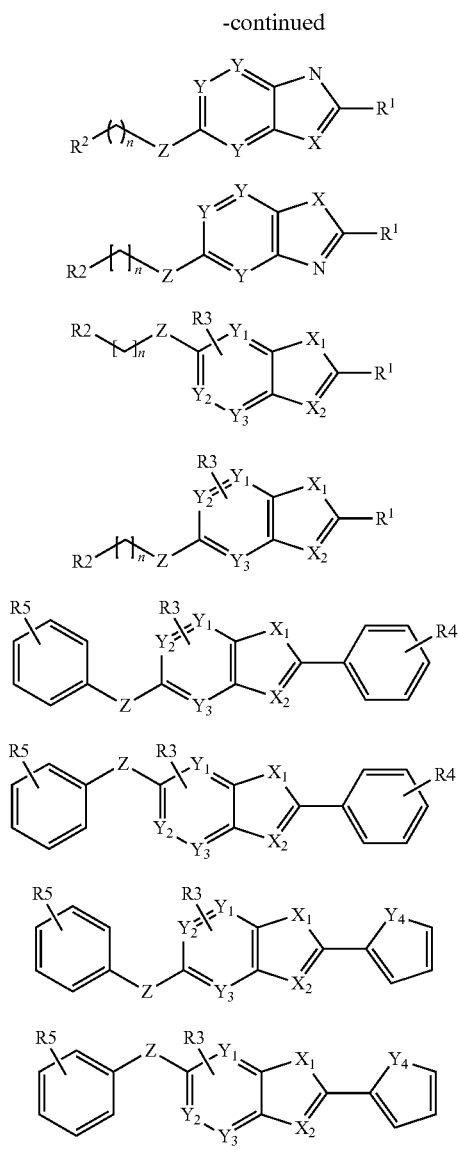

Formula B
Formula C
Formula D
Formula E
Formula F
Formula G
Formula H
Formula I

In Formula A: X and Y are independently selected from C, N, NH, N-alkyl, O, or S; and Z is an amide, amine, imine, urea, thiourea, or thioamide functional group (either constitutional isomer, where possible). In Formula A, X and Y are not both N-alkyl, O, S, or O and S together, N-alkyl and O together, or N-Alkyl and S together.

In Formulas B and C: X is independently selected from C, N, NH, N-alkyl, O, or S; Y is selected from C, or N; $R^1$ is a substituted or unsubstituted heterocycle selected from 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3)oxadiazole, 5-(1,2,3)oxadiazole, 4-(1,2,3)triazole, 5-(1,2,3)triazole, or 2-(1,3,4)thiadiazole; $R^2$ is a substituted or unsubstituted cycle or heterocycle selected from phenyl, 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3)oxadiazole, 5-(1,2,3)oxadiazole, 4-(1,2,3)triazole, 5-(1,2,3)triazole, or 2-(1,3,4)thiadiazole; Z is an amide, amine, imine, urea, thiourea, or thioamide functional group (either constitutional isomer, where possible); and n=0, 1, 2, or 3; where the substituted cycle or heterocycle is substituted at any position with H, a halogen, Cl, F, $CH_3$, $CH_3CH_2$, or higher or lower substituted or unsubstituted straight chain or branched aliphatic.

In Formulas D and E: $X_1$ and $X_2$ are independently selected from C, N, NH, N-alkyl, O, or S; $Y_1$, $Y_2$, and $Y_3$ are independently selected from C, or N; $R^1$ is a substituted or unsubstituted heterocycle selected from 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3)oxadiazole, 5-(1,2,3) oxadiazole, 4-(1,2,3)triazole, 5-(1,2,3)triazole, or 2-(1,3,4)thiadiazole; $R^2$ is a substituted or unsubstituted cycle or heterocycle selected from phenyl, 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3)oxadiazole, 5-(1,2,3) oxadiazole, 4-(1,2,3)triazole, 5-(1,2,3)triazole, or 2-(1,3,4) thiadiazole; $R^3$ is H, a halogen, Cl, F, Br, $NO_2$, $CH_3$, $CH_3CH_2$, or higher or lower substituted or unsubstituted straight chain or branched aliphatic; Z is an amide, amine, imine, urea, thiourea, or thioamide functional group (either constitutional isomer, where possible); and n=0, 1, 2, or 3; where the substituted cycle or heterocycle is substituted at any position with H, a halogen, Cl, F, Br, $NO_2$, $CH_3$, $CH_3CH_2$, or higher or lower substituted or unsubstituted aliphatic. In Formulas D and E, $X_1$ and $X_2$ are not both N-alkyl, O, S, or O and S together, N-alkyl and O together, or N-Alkyl and S together. $R^3$ can be a substituent on any ring atom.

In Formulas F and G: $X_1$ and $X_2$ are independently selected from C, N, NH, N-alkyl, O, or S; $Y_1$, $Y_2$, and $Y_3$ are independently selected from C, or N; $R^3$, $R^4$, and $R^5$ are independently selected from the group consisting of H, a halogen, Cl, F, Br, $NO_2$, $CH_3$, $CH_3CH_2$, or higher or lower substituted or unsubstituted straight chain or branched aliphatic; Z is an amide, amine, imine, urea, thiourea, or thioamide functional group (either constitutional isomer, where possible); and n=0, 1, 2, or 3; where $X_1$ and $X_2$ are not both N-alkyl, O, S, or O and S together, N-alkyl and O together, or N-Alkyl and S together. $R^3$, $R^4$, and/or $R^5$ can be a substituent on any ring atom.

In Formulas H and I: $X_1$ and $X_2$ are independently selected from C, N, NH, N-alkyl, O, or S; $Y_1$, $Y_2$, and $Y_3$ are independently selected from C, or N; $Y_4$ is selected from C, N, NH, N-alkyl, O, or S; each $R^3$ and $R^5$ are independently selected from the group consisting of H, a halogen, Cl, F, Br, $NO_2$, $CH_3$, $CH_3CH_2$, or higher or lower substituted or unsubstituted straight chain or branched aliphatic; Z is an amide, amine, imine, urea, thiourea, or thioamide functional group (either constitutional isomer, where possible); and n=0, 1, 2, or 3; where the substituted cycle or heterocycle is substituted at any position with H, amino acid, peptide, polypeptide, a halogen, Cl, F, Br, $NO_2$, $CH_3$, $CH_3CH_2$, or higher or lower substituted or unsubstituted aliphatic. In Formulas H and I, $X_1$ and $X_2$ are not both N-alkyl, O, S, or O and S together, N-alkyl and O together, or N-Alkyl and S together. $R^3$ and/or $R^5$ can be a substituent on any ring atom.

As used herein, the term "hetero atoms" is meant to refer to atoms other than carbon atoms such as oxygen, nitrogen, sulfur, phosphorus, and the like. Usually, a heteroatom is multivalent so as to form at least two covalent bonds, which can be used in a linking group or other moiety. Hetero atoms can be included in any ring or chain of any structure shown herein.

As used herein, the term "aliphatic" is meant to refer to a hydrocarbyl moiety, such as an alkyl group, that can be straight or branched, saturated or unsaturated, and/or substituted or unsubstituted, which has twenty or less carbons in the backbone. Any R group can be an aliphatic or any atom in a ring or chain can be substituted with an aliphatic. An aliphatic group may comprise moieties that are linear, branched, cyclic and/or heterocyclic, and contain functional groups such as ethers, ketones, aldehydes, carboxylates, and the like. Exemplary aliphatic groups include but are not limited to substituted and/or unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, alkyl groups of higher number of carbons and the like, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, and the like. The terms aliphatic or alkyl also encompasses alkenyl groups, such as vinyl, allyl, aralkyl and alkynyl groups.

Substitutions within an aliphatic group, or in R group or chain or ring atom, can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. The aliphatic groups can by way of example also comprise modifications such as azo groups, keto groups, aldehyde groups, carbonyl groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Additionally, the substitutions can be via single, double, or triple bonds, when relevant or possible.

Further, aliphatic groups may also contain hetero substitutions, which are substitutions of carbon atoms, by hetero atoms such as, for example, nitrogen, oxygen, phosphorous, or sulfur. As such, a linker comprised of a substituted aliphatic can have a backbone comprised of carbon, nitrogen, oxygen, sulfur, phosphorous, and/or the like. Heterocyclic substitutions refer to alkyl rings having one or more hetero atoms. Examples of heterocyclic moieties include but are not limited to morpholino, imidazole, and pyrrolidino.

As used herein, the term "aromatic" is meant to refer to molecule is one in which electrons are free to cycle around circular or cyclic arrangements of atoms, which are alternately singly and doubly bonded to one another. More properly, these bonds may be seen as a hybrid of a single bond and a double bond, each bond in the ring being identical to every other. Any R group can be an aromatic or any atom in a ring or chain can be substituted with an aromatic substituent. Examples of aromatic compounds that can be present in topiramate analogs include benzene, benzyl, toluene, xylene, and the like. The aromatic compound can include hetero atoms so as to be a hetero aromatic such as pyridine, furan, tetrahydrofuran, and the like. Also, an aromatic can be a polycyclic aromatic such as naphthalene, anthracene, phenanthrene, polycyclic aromatic hydrocarbons, indole, quinoline, isoquinoline, and the like.

As used herein, the term "amine" is meant to refer to moieties that can be derived directly or indirectly from ammonia by replacing one, two, or three hydrogen atoms by other groups, such as, for example, alkyl groups. Any R group can be an amine or any atom in a ring or chain can be substituted with an amine substituent. Primary amines have the general structures $RNH_2$ and secondary amines have the general structure $R_2NH$. The term amine includes, but is not limited to methylamine, ethylamine, propylamine, isopropylamine, aniline, cyclohexylamine, benzylamine, polycyclic amines, heteroatom substituted aryl and alkylamines, dimethylamine, diethylamine, diisopropylamine, dibutylamine, methylpropylamine, methylhexylamine, methylcyclopropyl amine, ethylcylohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

As used herein, the term "halo" or "halogen" means fluoro, chloro, bromo, or iodo, preferably fluoro and chloro.

As used herein, the term "poly(amino acid)" or "polypeptide" is a polyamide formed from amino acids. Poly(amino acid)s will generally range from about 200-2,000 molecular weight or greater than about 2,000 molecular weight, or having no upper molecular weight limit, and normally being less than 10,000,000 and usually not more than about 600,000 daltons. Any R group can be a polypeptide or any atom in a ring or chain can be substituted with a polypeptide substituent.

As used herein, the term "peptide" is meant to refer to any compound formed by the linkage of two or more amino acids by amide (peptide) bonds, usually a polymer of α-amino acids in which α-amino group of each amino acid residue (except the $NH_2$ terminus) is linked to the α-carboxyl group of the next residue in a linear chain; The terms "peptide," "polypeptide," and "poly(amino acid)" are used synonymously herein to refer to this class of compounds without restriction as to size. The largest members of this class are referred to as proteins.

Additionally, some of the compounds of the present invention can be prepared as racemic mixtures of isomers, mixtures of isomers, or optically isolated isomers. Compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", $4^{th}$ edition J. March, John Wiley and Sons, New York, 1992).

IV. Therapeutic Methods

The compounds of the present invention can be used for the treatment, inhibition, and/or prevention of cancer in a subject. This can include ovarian and/or breast cancer as well as other cancers. The ability of a compound of the present invention to modulate BRCA1 may provide for new therapeutic methods for cancer.

As used herein, the term "treating" or "treatment" of a disease, such as cancer, includes: (a) preventing the disease, i.e. causing the clinical symptoms of the disease not to develop in a mammal that may be exposed to or predisposed to the disease but does not yet experience or display symptoms of the disease; (b) inhibiting the disease, i.e., arresting or reducing the development of the disease or its clinical symptoms; or (c) relieving the disease, i.e., causing regression of the disease or its clinical symptoms. Inhibiting cancer can also include inhibiting cancer propagation. Prevention of cancer can include total prevention as well as a temporary prevention so as to delay onset. Inhibition and prevention can be useful for subject that have been identified to be susceptible to cancer via the identification of a mutant BRCA1 or insufficient amount or activity of BRCA1.

In one embodiment, a compound of the present invention can be administered to a subject that is susceptible to or has cancer, such as ovarian and/or breast cancer. As such, the treatment, inhibition, and/or prevention of breast and/or ovarian cancers can be performed by administering to a subject in need thereof an effective amount of a compound as described herein. Optionally, the compound can be administered in combination with a pharmaceutically acceptable additive, carrier or excipient. A patient that can be treated with a therapeutic method can be a subject that has been diagnosed to have a mutant BRCA1 gene or insufficient BRCA1 amount or activity. Also, the patient can be someone that has ovarian and/or breast cancer.

In one embodiment, a therapeutic method can include a method for inhibiting and/or preventing the growth of breast and/or ovarian cancers. Such a method can include identifying a subject to have a malignant tumor or cancer (e.g., breast and/or ovarian cancers), and then administering a compound of the present invention in an inhibitory or therapeutically effective amount or concentration.

The therapeutic methods can be used with one or more of the compounds described herein. Also, the compounds can be coadministered together or with other therapeutic compounds, such as other compounds that can be used in managing cancer. As such, the compounds of the present invention can be administered alone, in combination with each other, or they can be used in combination with other known compounds. For instance, the compounds can be used in conjunctive therapy with other known anti-angiogenic chemotherapeutic or antineoplastic agents (e.g., vinca alkaloids, antibiotics, antimetabolites, platinum coordination complexes, etc.). For instance, the compounds can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; or a platinum coordination complex, such as cisplatin (cis-DDP), carboplatin, etc. In addition, the compounds can be used in conjunctive therapy with other known anti-angiogenic chemotherapeutic or antineoplastic compounds.

As used herein, the term "coadmninistration" or "combination therapy" is used to describe a therapy in which at least two active compounds in effective amounts are used to treat breast and/or ovarian tumors. Although the term coadministration preferably includes the administration of two active compounds to the patient at the same time, it is not necessary that the compounds be administered to the patient at the same time, although effective amounts of the individual compounds will be present in the patient at the same time.

V. Pharmaceutical Compositions

Compounds according to the present invention may be used in pharmaceutical compositions having biological/pharmacological activity for the treatment of breast and/or ovarian cancers. These compositions comprise an effective amount of any one or more of the compounds disclosed herein, optionally in combination with a pharmaceutically acceptable additive, carrier, or excipient. Also, the compounds can be combined and/or prepared into pharmaceutically acceptable salts. The compounds may also be co-administered with other therapeutic agents, such as other compounds that modulate BRCA1. The effective amount can be a therapeutically effective amount of the compound sufficient for use in treating, inhibiting, and/or preventing cancer, such as breast and/or ovarian cancers, as well as other cancers.

As used herein, the terms "an effective amount", "therapeutic effective amount", or "therapeutically effective amount" shall mean an amount or concentration of a compound according to the present invention which is effective within the context of its administration or use. Thus, the term "effective amount" is used throughout the specification to describe concentrations or amounts of compounds according to the present invention which may be used to produce a favorable change in the disease or condition treated, whether that change is a remission, a decrease in growth or size of cancer or a tumor, a favorable physiological result, a reduction in the growth or elaboration of a microbe, or the like, depending upon the disease or condition treated.

As used herein, the term "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

As used herein, the term "pharmaceutically acceptable acid addition salts" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Groups which form pharmaceutically acceptable acid addition salts include amines, hydrazines, amidines, guanidines, substituted aryl/heteroaryl and substituted alkyl groups that carry at least a nitrogen bearing substituent such as amino, uanidine, amidino, uanidine and the like.

The compounds of the present invention can be formulated into a pharmaceutically acceptable formulation. Such a composition can be useful to prevent, alleviate, eliminate, or delay the onset of breast and/or ovarian cancers, and thereby can be used as an inhibitor, prophylactic, or treatment for breast and/or ovarian cancers.

In embodiments of the present invention, the pharmaceutical composition comprises an active component and inactive components. The active components are compounds described herein and their derivatives/analogues. The inactive components are selected from the group consisting of excipients, carriers, solvents, diluents, stabilizers, enhancers, additives, adhesives, and combinations thereof.

The amount of the compound in a formulation can vary within the full range employed by those skilled in the art. Typically, the formulation will contain, on a weight percent basis, from about 0.01-99.99 weight percent of the compounds of the present invention based on the total formulation, with the balance being one or more suitable pharmaceutical excipients. Preferably, the compounds are present at a level of about 1-80 weight percent.

Pharmaceutical preparations include sterile aqueous or non-aqueous solutions, suspensions and emulsions. Examples of non-aqueous solvents are propylene glycol, polyethylene glycol, vegetable oil such as olive oil, injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents and inert gases and the like. Those of skill in the art can readily determine the various parameters for preparing these pharmaceutical compositions without resort to undue experimentation.

Pharmacological compositions may be prepared from water-insoluble compounds, or salts thereof, such as aqueous base emulsions. In such embodiments, the pharmacological composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

Additionally, the compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate.

Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multi-dose use. Pharmacological agent compositions for use in practicing the subject methods may be lyophilized using techniques well known in the art.

The compositions may also include components, such as cyclodextrins, to enhance the solubility of one or more other components included in the compositions. Cyclodextrins are widely known in the literature to increase the solubility of poorly water-soluble pharmaceuticals or drugs and/or enhance pharmaceutical/drug stability and/or reduce unwanted side effects of pharmaceuticals/drugs. For example, steroids, which are hydrophobic, often exhibit an increase in water solubility of one order of magnitude or more in the presence of cyclodextrins. Any suitable cyclodextrin component may be employed in accordance with the present invention. The useful cyclodextrin components include, but are not limited to, those materials which are effective in increasing the apparent solubility, preferably water solubility, of poorly soluble active components and/or enhance the stability of the active components and/or reduce unwanted side effects of the active components. Examples of useful cyclodextrin components include, but are not limited to: β-cyclodextrin, derivatives of β-cyclodextrin, carboxymethyl-β-cyclodextrin, carboxymethyl-ethyl-β-cyclodextrin, diethyl-β-cyclodextrin, dimethyl-β-cyclodextrin, methyl-β-cyclodextrin, random methyl-β-cyclodextrin, glucosyl-β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof.

The specific cyclodextrin component selected should have properties acceptable for the desired application. The cyclodextrin component should have or exhibit reduced toxicity, particularly if the composition is to be exposed to sensitive body tissue, for example, eye tissue, etc. Very useful β-cyclodextrin components include β-cyclodextrin, derivatives of β-cyclodextrin and mixtures thereof. Particularly useful cyclodextrin components include sulfobutylether β-cyclodextrin, hydroxypropyl cyclodextrin and mixtures thereof. Sulfobutylether β-cyclodextrin is especially useful, for example, because of its substantially reduced toxicity.

The pharmaceutically acceptable excipients, such as vehicles, adjuvants, carriers or diluents, are readily available to the public. Examples of suitable excipients can include, but are not limited to, the following: acidulents, such as lactic acid, hydrochloric acid, and tartaric acid; solubilizing components, such as non-ionic, cationic, and anionic surfactants; absorbents, such as bentonite, cellulose, and kaolin; alkalizing components, such as diethanolamine, potassium citrate, and sodium bicarbonate; anticaking components, such as calcium phosphate tribasic, magnesium trisilicate, and talc; antimicrobial components, such as benzoic acid, sorbic acid, benzyl alcohol, benzethonium chloride, bronopol, alkyl parabens, cetrimide, phenol, phenylmercuric acetate, thimerosol, and phenoxyethanol; antioxidants, such as ascorbic acid, alpha tocopherol, propyl gallate, and sodium metabisulfite; binders, such as acacia, alginic acid, carboxymethyl cellulose, hydroxyethyl cellulose; dextrin, gelatin, guar gum, magnesium aluminum silicate, maltodextrin, povidone, starch, vegetable oil, and zein; buffering components, such as sodium phosphate, malic acid, and potassium citrate; chelating components, such as EDTA, malic acid, and maltol; coating components, such as adjunct sugar, cetyl alcohol, polyvinyl alcohol, carnauba wax, lactose maltitol, titanium dioxide; controlled release vehicles, such as microcrystalline wax, white wax, and yellow wax; desiccants, such as calcium sulfate; detergents, such as sodium lauryl sulfate; diluents, such as calcium phosphate, sorbitol, starch, talc, lactitol, polymethacrylates, sodium chloride, and glyceryl palmitostearate; disintegrants, such as colloidal silicon dioxide, croscarmellose sodium, magnesium aluminum silicate, potassium polacrilin, and sodium starch glycolate; dispersing components, such as poloxamer 386, and polyoxyethylene fatty esters (polysorbates); emollients, such as cetearyl alcohol, lanolin, mineral oil, petrolatum, cholesterol, isopropyl myristate, and lecithin; emulsifying components, such as anionic emulsifying wax, monoethanolamine, and medium chain triglycerides; flavoring components, such as ethyl maltol, ethyl vanillin, fumaric acid, malic acid, maltol, and menthol; humectants, such as glycerin, propylene glycol, sorbitol, and triacetin; lubricants, such as calcium stearate, canola oil, glyceryl palmitostearate, magnesium oxide, poloxymer, sodium benzoate, stearic acid, and zinc stearate; solvents, such as alcohols, benzyl phenylformate, vegetable oils, diethyl phthalate, ethyl oleate, glycerol, glycofurol, for indigo carmine, polyethylene glycol, for sunset yellow, for tartazine, triacetin; stabilizing components, such as cyclodextrins, albumin, xanthan gum; and tonicity components, such as glycerol, dextrose, potassium chloride, and sodium chloride; and mixture thereof. Excipients include those that alter the rate of absorption, bioavailability, or other pharmacokinetic properties of pharmaceuticals, dietary supplements, alternative medicines, or nutraceuticals.

Other examples of suitable excipients, binders and fillers are listed in Remington's Pharmaceutical Sciences, 18th Edition, ed. Alfonso Gennaro, Mack Publishing Co. Easton, Pa., 1995 and Handbook of Pharmaceutical Excipients, 3rd Edition, ed. Arthur H. Kibbe, American Pharmaceutical Association, Washington D.C. 2000, both of which are incorporated herein by reference.

In some embodiments, the compounds in the compositions may be present as a pharmaceutically acceptable salt. The term "pharmaceutically acceptable salts" includes salts of the composition, prepared, for example, with acids or bases, depending on the particular substituents found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galactunoric, salicylic, formic, naphthalene-2-sulfonic, and the like. Still other suitable acids include amino acids such as arginate, aspartate, glutamate, and the like.

In general, pharmaceutically acceptable carriers for are well-known to those of ordinary skill in the art. This carrier can be a solid or liquid and the type is generally chosen based on the type of administration being used. Suitable pharmaceutical carriers are, in particular, fillers, such as sugars, for example lactose, sucrose, mannitol or sorbitol, cellulose preparations and/or calcium phosphates, for example tricalcium phosphate or calcium hydrogen phosphate, furthermore, binders such as starch paste, using, for example, corn, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropyl-methylcellulose phthalate. Colorants or pigments, for example, to identify or to indicate different doses of active ingredient, may be added to the tablets or sugar-coated tablet coatings.

Additional pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Additional formulations for use in the present invention can be found in Remington's Pharmaceutical Sciences (Mack Publishing Company, Philadelphia, Pa., 17th ed. (1985)), which is incorporated herein by reference. Moreover, for a brief review of methods for drug delivery, see, Langer, Science 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. Other examples of suitable pharmaceuticals are listed in 2000 Med Ad News 19:56-60 and The Physicians Desk Reference, 53rd edition, 792-796, Medical Economics Company (1999), both of which are incorporated herein by reference.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. One manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of this invention is inhalation.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilizers.

Suitable rectally utilizable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 (herein incorporated by reference) describes a pharmaceutical formulation having particles in the size range from 10 to 1,000 nm in which the active material is supported on a crosslinked matrix of macromolecules. U.S. Pat. No. 5,145,684 (herein incorporated by reference) describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

According to the methods of the present invention, the compositions of the invention can be administered by injection by gradual infusion over time or by any other medically acceptable mode. Any medically acceptable method may be used to administer the composition to the patient. The particular mode selected will depend of course, upon factors such as the particular drug selected, the severity of the state of the subject being treated, or the dosage required for therapeutic efficacy. The methods of this invention, generally speaking, may be practiced using any mode of administration that is medically acceptable, meaning any mode that produces effective levels of the active composition without causing clinically unacceptable adverse effects.

The administration may be localized (i.e., to a particular region, physiological system, tissue, organ, or cell type) or systemic. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be used for some treatments because of the convenience to the patient as well as the dosing schedule. Compositions suitable for oral administration may be presented as discrete units such as capsules, pills, cachettes, tables, or lozenges, each containing a predetermined amount of the active compound. Other oral compositions include suspensions in aqueous or non-aqueous liquids such as syrup, an elixir, or an emulsion.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as tale or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds can be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulator agents such as suspending, stabilizing and/or dispersing agents.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds can be encapsulated in a vehicle such as liposomes that facilitates transfer of the bioactive molecules into the targeted tissue, as described, for example, in U.S. Pat. No. 5,879,713 to Roth et al. and Woodle, et al., U.S. Pat. No. 5,013,556, the contents of which are hereby incorporated by reference. The compounds can be targeted by selecting an encapsulating medium of an appropriate size such that the medium delivers the molecules to a particular target. For example, encapsulating the compounds within microparticles, preferably biocompatible and/or biodegradable microparticles, which are appropriate sized to infiltrate, but remain trapped within, the capillary beds and alveoli of the lungs can be used for targeted delivery to these regions of the body following administration to a patient by infusion or injection.

Microparticles can be fabricated from different polymers using a variety of different methods known to those skilled in the art. The solvent evaporation technique is described, for example, in E. Mathiowitz, et al., J. Scanning Microscopy, 4, 329 (1990); L. R. Beck, et al., Fertil. Steril., 31, 545 (1979); and S. Benita, et al., J. Pharm. Sci., 73, 1721 (1984). The hot-melt microencapsulation technique is described by E. Mathiowitz, et al., Reactive Polymers, 6, 275 (1987). The spray drying technique is also well known to those of skill in the art. Spray drying involves dissolving a suitable polymer in an appropriate solvent. A known amount of the compound is suspended (insoluble drugs) or co-dissolved (soluble drugs) in the polymer solution. The solution or the dispersion is then spray-dried. Microparticles ranging between 1-10 microns are obtained with a morphology which depends on the type of polymer used.

Microparticles made of gel-type polymers, such as alginate, can be produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath to allow sufficient time for gelation to occur. Microparticle particle size is controlled by using various size extruders or varying either the nitrogen gas or polymer solution flow rates.

Particle size can be selected according to the method of delivery which is to be used, typically size IV injection, and where appropriate, entrapment at the site where release is desired.

In one embodiment, the liposome or microparticle has a diameter which is selected to lodge in particular regions of the body. For example, a microparticle selected to lodge in a capillary will typically have a diameter of between 10 and 100, more preferably between 10 and 25, and most preferably, between 15 and 20 microns. Numerous methods are known for preparing liposomes and microparticles of any particular size range. Synthetic methods for forming gel microparticles, or for forming microparticles from molten materials, are known, and include polymerization in emulsion, in sprayed drops, and in separated phases. For solid materials or preformed gels, known methods include wet or dry milling or grinding, pulverization, classification by air jet or sieve, and the like.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, injection etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert at least one pharmacological agent into the delivery device for administration of the pharmacological agent to a subject and include, but are not limited to, vials, ampules, tubes, capsules, bottles, syringes and bags.

Sterile injectable forms of the compositions of this invention may be aqueous or a substantially aliphatic suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. Pharmacological agent formulations suitable for transdermal administration may also be delivered by iontophoresis and may take the form of an optionally buffered aqueous solution of the pharmacological agent compound. Suitable formulations may include citrate or bis/tris buffer (pH 6) or ethanol/water and contain a suitable amount of active ingredient. Topical application for the lower intestinal tract can be effected in a rectal suppository formulation (see above) or in a suitable enema formulation. Topically-transdermal patches may also be used.

For other topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Depending on the mode of administration, the pharmaceutical composition will preferably comprise from 0.05 to 99% by weight, more preferably from 0.1 to 70% by weight of the active ingredient, and, from 1 to 99.95% by weight, more preferably from 30 to 99.9% by weight of a pharmaceutically acceptable carrier, all percentages being based on the total composition.

The compositions of the present invention may be given in dosages, generally at the maximum amount while avoiding or minimizing any potentially detrimental side effects. The compositions can be administered in effective amounts, alone or in a cocktail with other compounds, for example, other compounds that can be used to treat and/or prevent breast and/or ovarian cancer. An effective amount is generally an amount sufficient to inhibit breast and/or ovarian cancer within the subject.

In one embodiment of the present invention, therapeutically effective amounts of compounds of the present invention may range from approximately 0.05 to 50 mg per kilogram body weight of the recipient per day; preferably about 0.01-25 mg/kg/day, more preferably from about 0.5 to 10 mg/kg/day. Thus, for administration to a 70 kg person, the dosage range would most preferably be about 35-70 mg per day.

In another embodiment of the present invention, dosages may be estimated based on the results of experimental models, optionally in combination with the results of assays of the present invention. Generally, daily oral doses of active compounds will be from about 0.01 mg/kg per day to 2000 mg/kg per day. Oral doses in the range of 10 to 500 mg/kg, in one or several administrations per day, may yield suitable results. In the event that the response of a particular subject is insufficient at such doses, even higher doses (or effective higher doses by a different, more localized delivery route) may be employed to the extent that patient tolerance permits. Multiple doses per day are also contemplated in some cases to achieve appropriate systemic levels of the composition. Dosage amount and interval may be adjusted individually to provide plasma levels of the active compound which are sufficient to maintain therapeutic effect. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

Although the exact dosage will be vary dependent upon the percent composition of the dosage of compounds of the present invention, in most cases some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro and in vivo data. Dosages necessary to achieve the MEC will depend on individual characteristics and route of administration. However, HPLC assays or bioassays can be used to determine plasma concentrations.

Use of a long-term release implant may be particularly suitable in some cases. "Long-term release," as used herein, means that the implant is constructed and arranged to deliver therapeutic levels of the composition for at least 30 or 45 days, and preferably at least 60 or 90 days, or even longer in some cases. Long-term release implants are well known to those of ordinary skill in the art, and include some of the release systems described above.

Any suitable dosage may be administered. The compound, the carrier, and the amount will vary widely depending on body weight, the severity of the condition being treated and other factors that can be readily evaluated by those of skill in the art. Generally a dosage of between about 1 mg per kg of body weight and about 100 mg per kg of body weight is suitable.

In pharmaceutical dosage forms, agents may be administered alone or with an appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time. The pharmacological agent and at least one other adjuvant may be administered simultaneously (i.e., concurrently) or sequentially. Simultaneous administration may be carried out by mixing at least one pharmacological agent and at least one other adjuvant prior to administration, or by administering the pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population), the $ED_{50}$ (the dose therapeutically effective in 50% of the population), and $EC_{50}$ (the excitatory concentration effective in 50% of the population). The dose ratio between toxic and therapeutic effect is the therapeutic index and can be expressed as the ratio between $LD_{50}$ and $ED_{50}$. Compounds which exhibit high therapeutic indices are candidates for further development. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: "The Pharmacological Basis of Therapeutics", Ch. 1, p. 1). Additionally, the $EC_{50}$ can be important to measure.

In one embodiment, a catheter is used to direct the composition directly to the location of the targeted tumor. As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

The exact formulation, route of administration and dosage for the pharmaceutical compositions of the present invention can be chosen by the individual physician in view of the patient's condition. (See e.g., et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $EC_{50}$, $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

EXAMPLES

1.

The human BRCA1 promoter was amplified from human genomic DNA (Promega, Madison, Wis.) with polymerase chain reaction (PCR). The primers encompass both the α- and β-promoters, resulting in an 1197 bp fragment (position 1068-2264, accession no. U37574). The primers used were based on previously defined promoter endpoints. Additionally, restriction cut sites for Acc65 I and Xho I were incorporated in the 5' and 3' ends, respectively. The PCR product was purified using the QIAquick Gel Extraction Kit (Qiagen, Valencia, Calif.) and digested for 1 hour at 37° C. prior to ligation with the reporter vector pGL4.14.

2.

The pGL4 Luciferase Reporter Vector was purchased from Promega. This vector contains the synthetic firefly luc2 (*Photinus pyralis*), the ampicillin (Amp$_r$) gene and the mammalian selectable marker gene for hygromycin (Hyg$_r$). Competent JM109 cells (Promega) were transformed with 0.1 µg of pGL4.14 DNA for 10 minutes on ice, followed by 50 second incubation at 42° C. and 60 minute incubation at 37° C. The transformed cells were spread on LB+ampicillin plates and incubated overnight at 37° C. Surviving colonies were selected and plasmid DNA was purified using the HiSpeed Plasmid Midi Kit (Qiagen). Plasmid DNA was digested with Acc65 I and Xho I for 1 hour at 37° C. (New England BioLabs, Ipswich, Mass.). The digested plasmid DNA and the digested PCR product containing the BRCA1 promoter were ligated with T4 DNA ligase (NEB) at 4° C. overnight. Isolated clones were verified by sequencing. MCF7 cells ($5 \times 10_6$) were transfected with 1 ptg of pGL4.14-hBRCA DNA using the Effectene Transfection Reagent per manufacturer's protocol for 48 hours (Qiagen). Transfected MCF7 cells were selected with hygromycin B (Mediatech).

3.

The human epithelial mammary gland adenocarcinoma MCF7 cell line was purchased from ATCC(HTB-22, Manassas, Va.). These estrogen receptor positive cells were cultured in Minimum essential medium (Eagle) with Earle's salts (Mediatech, Herndon, Va.), containing 10% fetal bovine serum (Cambrex Bio Science, Rockland, Me.), 50 U/ml each of penicillin and streptomycin (Mediatech) and 2 mM L-glutamine (Mediatech) at 37° C., 5% $CO_2$ humidified atmosphere. Following transfection these cells were additionally maintained in 50 μg/ml Hygromycin B (Mediatech).

The human BRCA1 promoter was cloned and inserted upstream of the firefly luciferase gene in the plasmid pGL4.14 (Promega). This construct allowed the detection of luciferase activity as the read-out for BRCA1 gene expression. The primers used to amplify the human promoter were based on previously defined promoter endpoint. These primers encompass both the α- and β-promoters, resulting in an 1197 bp fragment (position 1068-2264, accession no. U37574), as discussed above. The plasmid pGL4.14 also contains a hygromycin resistance marker, allowing for the generation of stable MCF7 cell lines expressing the human BRCA1-luciferase reporter construct. MCF7 cells are human breast cancer cells that are estrogen receptor positive. These cells serve as our model system because it was observed that patients with sporadic breast cancer who expressed BRCA1 also expressed estrogen receptor.

Hygromycin selected MCF7 cells were seeded in 384-well tissue culture plates. The first two columns of each plate were empty so as to include established positive and negative controls. Each of the remaining 352 wells contained a compound to be screened. MCF7 cells were incubated with the compounds for 48 hours. Luciferase activity was measured using the Steady Glo Luciferase Assay System (Promega). Briefly, $5 \times 10^6$ MCF7 cells were transfected with 1 mg of purified pGL4.14 containing the human BRCA1 promoter (pGL4.14-hBRCA) with Effectene as per manufacturers protocol (Qiagen). Stable transfectants were selected with 50 mg/ml Hygromicin B. $1 \times 10^5$ or $2 \times 10^5$ stable transfectants were tested for luciferase activity with the Steady-Glo Luciferase Assay System (Promega).

FIG. 1 shows the relative luciferase light units of the clones, which indicates that MCF7 clone pGL4.14-H-1 is superior.

5.

Subclones of pGL4.14-hBRCA-1 were tested to determine an optimal assays system. Briefly, pGL4.14-hBRCA-1 stable clone was further subcloned and 12 colonies were expanded and tested for luciferase activity. Hygromycin selected MCF7 cells were seeded in 384-well white tissue culture plates (Becton Dickenson, San Diego, Calif.) at various cell concentrations. Indicated numbers of stable transfectants were tested for luciferase activity with the Steady-Glo Luciferase Assay System.

FIG. 2 shows the relative luciferase light units of the clones, which indicates that MCF7 clone pGL4.14-H-1.3 is superior.

6.

Hygromycin selected MCF-7 cells (e.g., MCF7 clone pGL4.14-hBRCA1.3) stably transfected with the human BRCA1-luciferase reporter construct (e.g., pGL4.14-hBRCA1.3) were seeded in 384-well white tissue culture plates (Becton Dickenson, San Diego, Calif.) at $1 \times 10^4$ cells/well. These cells were then stimulated with indicated concentrations of genistein (Sigma-Aldrich, St. Louis, Mo.) for 0, 6, 9, 24 and 48 hours. Luciferase activity was measured using the Steady Glo Luciferase Assay System (Promega). The data shown in FIG. 3A is representative of 3 individual experiments. FIG. 3B shows BRCA1 protein expression of genistein, with lane 1 being non-stimulated, lane 2 being DMSO treated, lane 3 being genistein at 1 uM, lane 4 being genistein at 10 uM, and lane 5 being genistein at 30 uM.

7.

Two different chemical libraries were screened for the ability to enhance BRCA1 gene expression. To examine the effects of each compound on BRCA1 expression, the human BRCA1 promoter was cloned and inserted upstream of the firefly luciferase gene in the plasmid pGL4.14 (BRCA1-Luc) (Promega), as described above. The ER positive human breast cancer cell line, MCF7, was transfected and stable transfectants were selected with hygromycin. Prior to screening the chemical libraries, it was determined that the vehicle, 2.5% DMSO, did not affect the attachment, growth or survival of MCF7 cells in 384 well plates (data not shown). Additionally, treatment of the stable MCF7 clone 1.3 with 10 μM genistein for 48 hours resulted in an increase in BRCA1-luciferase activity (FIG. 3A) and therefore, served as the positive control for each plate of compounds under evaluation.

Six hundred and sixty two compounds were "hits" that increased BRCA1 expression greater than 2 standard deviations above the control (data not shown). The compounds identified as hits were further tested for activity in luciferase light units, for EC50, and for toxicity (e.g., cell viability).

Briefly, compounds were plated in a 384 well plate in a total volume of 20 μl. A ten point dilution series was used at concentrations—100 M, 10 μM, 1 μM, 100 nM, 10 nM, 1 nM, 0.1 nM, 0.01 nM, 0.0001 nM, 0 (DMSO vehicle only). A second dilution series of 100 μM, 32.5 μM, 10.8 M, 3.6 μM, 1.2 μM, 400 nM, 132.2 nM, 45 nM, 14.8 nM, 5 nM, and 1.65 nM was also used. MCF7-BRCA1-luciferase cells were added to the compounds at a concentration of $1 \times 10^4$ cells/well in a volume of 25 μl. The 384 well plates, containing the compounds+cells, were then incubated at 37° C. for 48 hours. After 48 hours, luciferase activity was measured with the Steady-Glo® Luciferase Assay System (Promega, Madison, Wis.).

Additionally, the compounds were tested for cell viability. Compounds were plated at 2x in 50 μl MEM in triplicate in a clear 96 well tissue culture plate. A ten point dilution series was used at concentrations—100 μM, 10 μM, 1 μM, 100 nM, nM, 1 nM, 0.1 nM, 0.01 nM, 0.0001 nM, 0 (DMSO vehicle only). MCF7 cells ($5 \times 10^3$) were added in a volume of 50 μl MEM to the appropriate wells, diluting the compounds to 1x. Cells were incubated at 37° C. for 48 hours. 20 μl of CellTiter 96® AQueous One Solution Reagent (Promega) was added to each well and incubated for 3 hours at 37° C. Absorbance was measured at 490 nM using the Perkin Elmer Victor 3V plate reader. Absorbance signals were normalized to DMSO vehicle control and were expressed as percent viable.

FIG. 4A shows that Compounds 1 and 2 were similar to genistein in activity. However, FIG. 4B shows that Compounds 1 and 2 were less toxic compared to genistein. The structures of genistein, Compound 1, and Compound 2 are shown below.

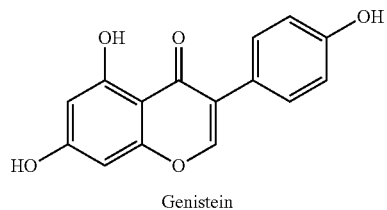

Genistein

Compound 1

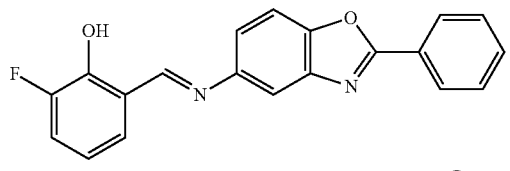

Compound 2

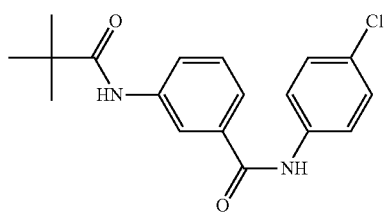

FIG. 5A shows the ability to increase BRCA1 by increasing the luciferase activity with Compounds 3, 4, 5, and 6. Compound 3 is shown to be comparatively superior. FIG. 5B shows the cytotoxicity of Compounds 3, 4, 5, and 6. The structures of Compounds 3, 4, 5, and 6 are shown below.

Compound 3

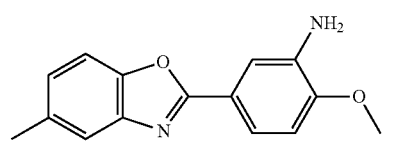

Compound 4

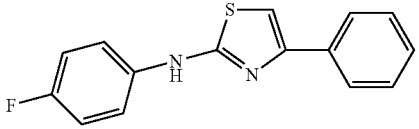

Compound 5

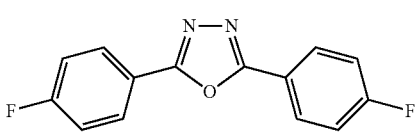

Compound 6

FIG. 6A shows the ability to increase BRCA1 by increasing the luciferase activity with Compounds 7, 8, 9, and 10. Compound 9 is shown to be comparatively superior, but similar to Compound 8 and 10. FIG. 6B shows the cytotoxicity of Compounds 7, 8, 9, and 10. The structures of Compounds 7, 8, 9, and are shown below.

Compound 7

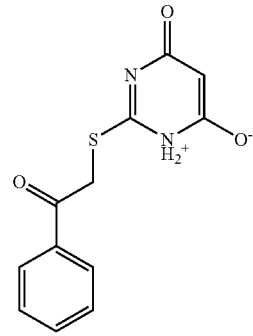

Compound 8

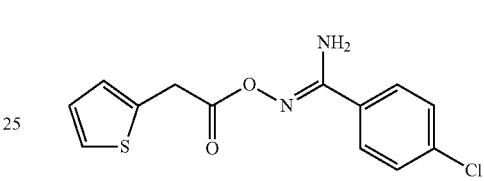

Compound 9

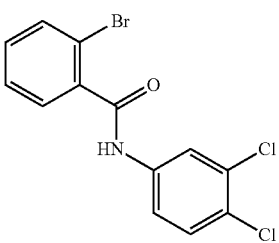

Compound 10

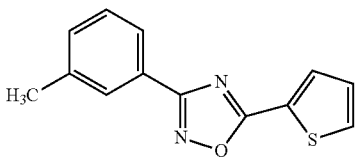

FIG. 7A shows the ability to increase BRCA1 by increasing the luciferase activity with Compounds 11, 12, 13, and 14. Compounds 11, 12, and 14 are shown to be comparatively superior to Compound 13. FIG. 7B shows the cytotoxicity of Compounds 11, 12, 13, and 14. The structures of Compounds 11, 12, 13, and 14 are shown below.

Compound 11

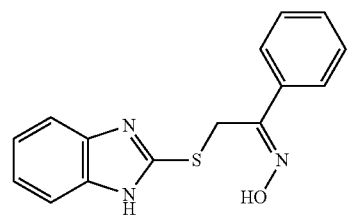

Compound 12

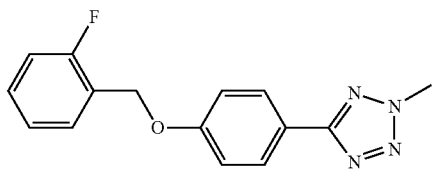

Compound 17

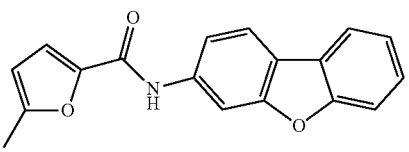

Compound 13

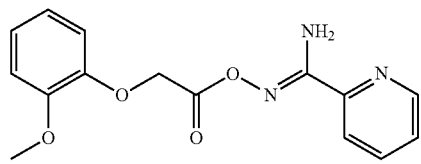

Compound 18

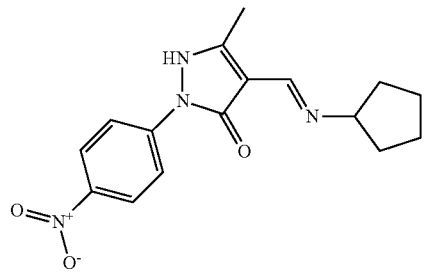

Compound 14

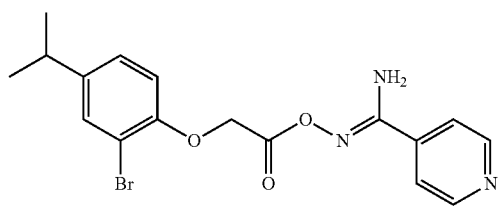

Compound 19

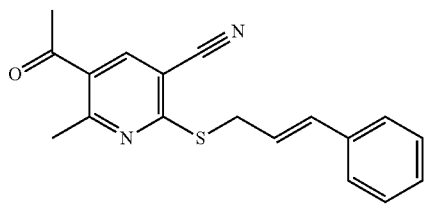

FIG. 8A shows the ability to increase BRCA1 by increasing the luciferase activity with Compounds 15 and 16. FIG. 8B shows the cytotoxicity of Compounds 15 and 16. The structures of Compounds 15 and 16 are shown below.

Compound 20

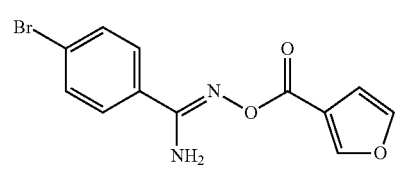

Compound 15

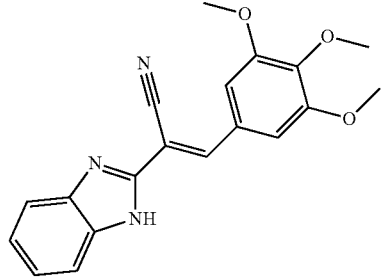

Compound 16

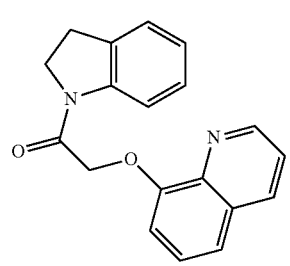

FIG. 10A shows the ability to increase BRCA1 by increasing the luciferase activity with Compounds 21, 22, 23, and 24. FIG. 10B shows the cytotoxicity of Compounds 21, 22, 23, and 24. The structures of Compounds 21, 22, 23, and 24 are shown below.

Compound 21

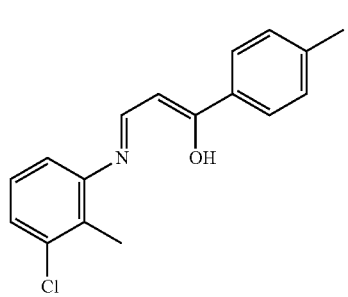

FIG. 9A shows the ability to increase BRCA1 by increasing the luciferase activity with Compounds 17, 18, 19, and 20. FIG. 9B shows the cytotoxicity of Compounds 17, 18, 19, and 20. The structures of Compounds 17, 18, 19, and 20 are shown below.

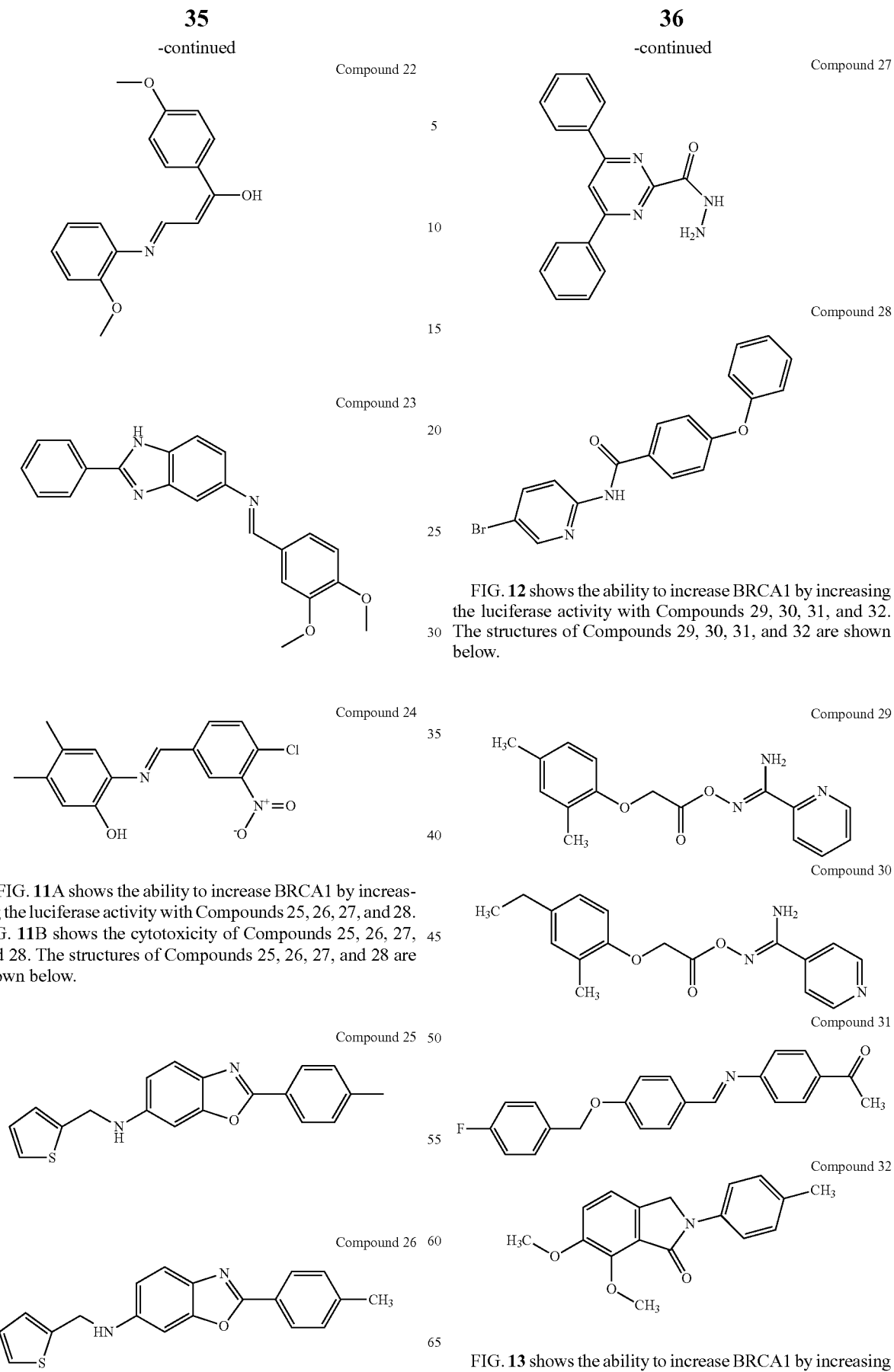

FIG. 12 shows the ability to increase BRCA1 by increasing the luciferase activity with Compounds 29, 30, 31, and 32. The structures of Compounds 29, 30, 31, and 32 are shown below.

FIG. 11A shows the ability to increase BRCA1 by increasing the luciferase activity with Compounds 25, 26, 27, and 28. FIG. 11B shows the cytotoxicity of Compounds 25, 26, 27, and 28. The structures of Compounds 25, 26, 27, and 28 are shown below.

FIG. 13 shows the ability to increase BRCA1 by increasing the luciferase activity with Compounds 33 (i.e., JN1-68), 34

(i.e., JN1-72), 35 (i.e., JN1-76), 36 (i.e., JN1-77), 37 (i.e., JN1-78), and 38 (i.e., JN1-82). The structures of Compounds 33, 34, 35, 36, 37, and 38 are shown below.

Compound 33

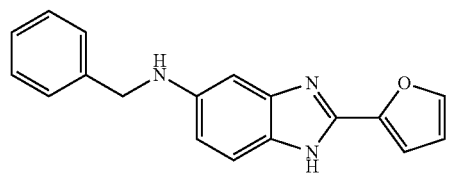

(i.e., JN1-68)

Compound 34

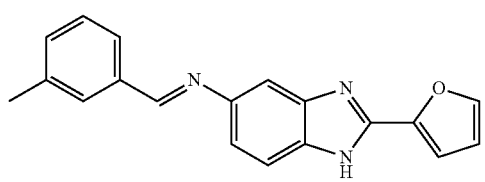

(i.e., JN1-72)

Compound 35

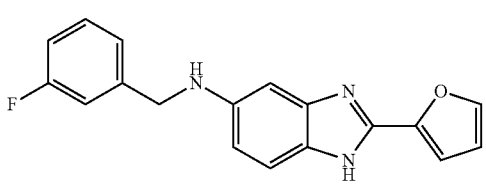

(i.e., JN1-76)

Compound 36

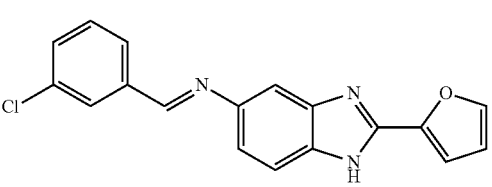

(i.e., JN1-77)

Compound 37

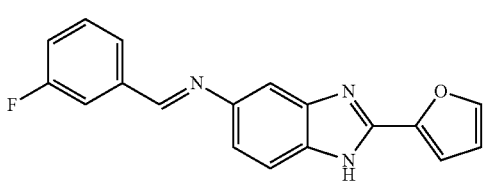

(i.e., JN1-78)

Compound 38

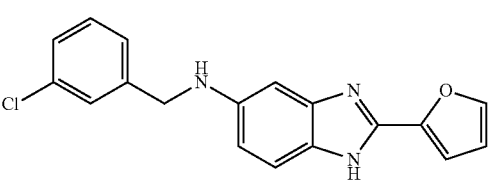

(i.e., JN1-82)

The EC50 is shown in Table 1.

TABLE 1

|  | $EC_{50}$ |
| --- | --- |
| Cmpd 10 | 2.18E−07 |
| Cmpd 4 | 7.29E−07 |
| Cmpd 17 | 9.48E−07 |
| Cmpd 9 | 1.30E−06 |
| Cmpd 6 | 1.64E−06 |
| Cmpd 12 | 1.67E−06 |
| JN1-82 | 2.05E−06 |
| JN1-76 | 2.42E−06 |
| JN1-68 | 3.53E−06 |
| Cmpd 30 | 4.13E−06 |
| Cmpd 31 | 4.88E−06 |
| Cmpd 11 | 6.77E−06 |
| Cmpd 1 | 6.82E−06 |
| Cmpd 28 | 6.96E−06 |
| Cmpd 29 | 8.49E−06 |
| Cmpd 25 | 8.63E−06 |
| Cmpd 3 | 8.73E−06 |
| Cmpd 32 | 9.43E−06 |
| Cmpd 23 | 1.07E−05 |
| Cmpd 22 | 1.10E−05 |
| Cmpd 21 | 1.12E−05 |
| Cmpd 18 | 1.12E−05 |
| Cmpd 5 | 1.16E−05 |
| Genistein | 1.45E−05 |
| JN1-78 | 1.74E−05 |
| Cmpd 19 | 2.06E−05 |
| JN1-72 | 2.58E−05 |
| Cmpd 26 | 2.87E−05 |
| JN1-77 | 3.49E−05 |
| Cmpd 20 | 5.03E−05 |
| Cmpd 13 | 6.96E−05 |
| Cmpd 2 | 7.05E−05 |
| Cmpd 14 | 1.06E−04 |
| Cmpd 7 | 2.06E−03 |
| Cmpd 8 | 2.15E−03 |
| Cmpd 27 | 3.57E+33 |
| Cmpd 24 | Value too large |
| Cmpd 15 | ND |
| Cmpd 16 | ND |

The EC90 is shown in Table 2.

TABLE 2

|  | $EC_{90}$ |
| --- | --- |
| Cmpd 24 | 3.45E−11 |
| Cmpd 27 | 1.86E−09 |
| Cmpd 4 | 1.77E−06 |
| Cmpd 10 | 2.56E−06 |
| Cmpd 17 | 2.85E−06 |
| JN1-82 | 4.94E−06 |
| JN1-76 | 5.94E−06 |
| JN1-68 | 8.84E−06 |
| Cmpd 9 | 1.01E−05 |
| Cmpd 12 | 1.58E−05 |
| Cmpd 18 | 1.72E−05 |
| Cmpd 22 | 2.07E−05 |
| Cmpd 6 | 2.42E−05 |
| Genistein | 2.50E−05 |
| Cmpd 32 | 4.68E−05 |
| Cmpd 3 | 4.73E−05 |
| JN1-78 | 4.94E−05 |
| Cmpd 1 | 5.49E−05 |
| Cmpd 30 | 5.54E−05 |
| Cmpd 31 | 7.15E−05 |
| Cmpd 19 | 7.94E−05 |
| Cmpd 11 | 8.05E−05 |
| Cmpd 29 | 9.18E−05 |
| JN1-72 | 1.10E−04 |
| Cmpd 20 | 1.70E−04 |
| JN1-77 | 1.96E−04 |
| Cmpd 26 | 3.66E−04 |
| Cmpd 13 | 3.77E−04 |

TABLE 2-continued

|  | $EC_{90}$ |
| --- | --- |
| Cmpd 2 | 9.67E-04 |
| Cmpd 14 | 9.98E-04 |
| Cmpd 7 | ~0.06371 |
| Cmpd 23 | ~1.177e-005 |
| Cmpd 5 | ~1.375e-005 |
| Cmpd 8 | ~2.353 |
| Cmpd 16 | ~3.880e-005 |
| Cmpd 21 | ~9.724e-006 |
| Cmpd 15 |  |
| Cmpd 25 |  |
| Cmpd 28 |  |

The secondary screens were performed to verify the positive hits identified in the primary screen. Out of the first 32 compounds tested, 27 of them responded in a dose-dependent manner and had a significant increase in BRCA1-luciferase activity. Several compounds did not significantly increase BRCA1-Luciferase activity. As expected, the positive controls, Genistein and Daidzein, demonstrated a dose-dependent increase in BRCA1-luciferase activity. This data also established the concentration of the compound that resulted in the greatest increase in BRCA1-luciferase activity ($EC_{50}$).

Select analogues were prepared as described herein and also showed increased BRCA1-luciferase activity in a dose-dependent manner (FIG. 13). Specifically, Compound 38 (i.e., JN1-82), Compound 35 (i.e., JN1-76), and Compound 33 (i.e., JN1-68) rank with the other top compounds and genistein.

The cell viability data is important to demonstrate that the tested compounds are not toxic to the cells.

8.

Compounds 29 and 30 were studied for BRCA1 and actin (e.g., housekeeping gene for normalization) protein expression. Briefly, MCF7 cells ($2\times10^6$) in 2 ml MEM were plated in a 6 well tissue culture plate and were either left nonstimulated or treated with DMSO (vehicle control), 10 M Genistein, or 3 different concentrations of indicated test compound—3.65 μM, 10.8 M, 32.5 μM. Following incubation at 37° C. for 48 hours, the media was removed and the cells were washed 1× with 500 μl of ice cold PBS. Another 500 μl of ice cold PBS was then added and the cells were scraped off the well and transferred to a microcentrifuge tube. To ensure all cells were removed from the well, an additional 500l of ice cold PBS was added to the well and any remaining cells were combined with the initial cell harvest into the microcentrifuge tube. The cells were then pelleted by centrifugation for 5 min at 3000 rpm, 4° C. The supernate was removed and the pellet was then lysed in 150 μl of ice cold RIPA buffer+1× protease inhibitors, on ice for 30 minutes, vortexing occasionally. The cellular debris was then removed by centrifugation for 20 minutes at 11,000 rpm, 4° C. The remaining supernate, containing the extracted proteins, was then transferred to a microcentrifuge tube and quantified using the Bio-Rad DC assay. 100 μg of protein+1×SDS-PAGE sample buffer was loaded onto an 8% Tris glycine gel. The proteins were separated in a tris glycine running buffer at 125 volts for 90 minutes. The proteins were then transferred out of the gel onto PVDF in an overnight transfer with 20% methanol at 35 volts, 4° C. The PVDF membrane was then blocked with 5% milk/PBST (0.1%) for 1 hour at room temperature (RT). BRCA1 protein was detected using anti-BRCA1 (Ab-1, EMD Biosciences) at a 1:250 dilution in 3% milk/PBST, overnight at 4° C. Following incubation with the primary antibody, the blot was washed 1×15 min, 3×5 min in PBST at RT. The blot was then incubated with GAM-HRP, the secondary antibody, at 1:5,000 in 3% milk/PBST for 1 hr at RT. To monitor equal protein loading, actin was detected using anti-actin at a 1:200,000 dilution in 5% milk/PBST for 1 hr at RT. Following incubation with the primary antibody, the blot was washed 1×15 min, 3×5 min in PBST at RT. The blot was then incubated with GAM-HRP, the secondary antibody, at 1:10,000 in 3% milk/PBST for 1 hr at RT. Prior to chemiluminescent detection the blots were washed 1×15 min, 3×5 min in PBST and 2×5 min in PBS. Chemiluminescence was detected using the SuperSignal West Femto kit made by Pierce Biotechnology and the UVP imaging center.

FIG. 14A shows BRCA1 protein expression compared to DMSO and genistein for Compound 29. Briefly, 100 μg of protein from MCF7 cells was separated after the following stimulation: Lane 1 was Non-Stimulated; Lane 2 was DMSO; Lane 3 was Genistein at 10 μM; Lane 4 was Compound 29 at 3.6 μM; Lane 5 was Compound 29 at 10.8 μM; and Lane 6 was Compound 29 at 32.5 μM.

FIG. 15A shows BRCA1 protein expression compared to DMSO and genistein for Compound 30. Briefly, 100 μg of protein from MCF7 cells was separated after the following stimulation: Lane I was Non-Stimulated; Lane 2 was DMSO; Lane 3 was Genistein at 10 μM; Lane 4 was Compound 30 at 3.6 μM; Lane 5 was Compound at 10.8 μM; and Lane 6 was Compound 30 at 32.5 μM.

The data indicates these compounds increase BRCA1 already present in the MCF7 cells. Compounds 29 and 30 increase endogenous BRCA1.

9.

Compounds 29 and 30 were studied for BRCA1 and 18S (e.g., housekeeping gene for normalization) RNA expression. Briefly, MCF7 cells ($2\times10^6$) in 2 ml MEM were plated in a 6 well tissue culture plate and were either left nonstimulated or treated with DMSO (vehicle control), 10 μM Genistein, or 3 different concentrations of indicated test compound—3.65 μM, 10.8 μM, 32.5 μM. Following incubation at 37° C. for 48 hours, the media was removed and RNA was extracted per manufacturer's protocol using the RNeasy Plus RNA extraction kit made by Qiagen. Complementary DNA (cDNA) was generated per manufacturer's protocol from 1000 ng extracted RNA in a 60 μl volume using the High Capacity cDNA kit made by Applied Biosystems. Gene expression of BRCA1 and 18S was detected with the TaqMan Gene Expression assay kit made by Applied Biosystems. The PCR reaction was set up as follows: 9 μl cDNA+10 μl TaqMan master mix+1 μl specific primer/probe set (BRCA1 and 18S). The 20l reaction was run on either the ABI real time system 7500 or 7000 (see, Analysis of Relative Gene Expression Data Using Real-Time Quantitative PCR and the $2^{-\Delta\Delta C_T}$ Method. Kenneth J. Livak[a] and Thomas D. Schmittgen[b, 1]. [a] Applied Biosystems, Foster City, Calif., 94404 [b] Department of Pharmaceutical Sciences, College of Pharmacy, Washington State University, Pullman, Wash., 99164-6534. Methods, Volume 25, Issue 4, December 2001, Pages 402-408).

FIG. 14B shows BRCA1 RNA expression compared to DMSO and genistein for Compound 29. FIG. 15B shows BRCA1 RNA expression compared to DMSO and genistein for Compound 30. Both Compounds 29 and 30 increase BRCA1 RNA expression.

10.

A Comparative Molecular Field Analysis (CoMFA) study was used to suggest a preliminary pharmacophore model. In order to ensure development of the most meaningful SAR model, the selection threshold for putative BRCA1 activators was amplified to 11 times greater than the screening-activity data-set mean, at which point clustering algorithms (e.g., DiverseSolutions bioactive subset selection method) resolved statistically significant differences in the profile of bioactive and inactive species. Within the resulting set of 39 compounds, one dominant cluster of 13 chemically similar species was identified (via Jarvis-Patrick clustering). Spatially aligning these 13 actives with a set of 15 chemically similar inactive species, the CoMFA model was trained via partial least square sitting, to achieve strong correlative and predictive capacity ($R_2$=0.98, $Q_2$ (leave-one-out)=0.77, $Q_2$ (five-fold cross-validation)=0.71 for a four component model). FIG. 16 shows a subset of the representative lead structures and shows 3 structures (e.g., Compound 22, Compound 23, and Analog of Compound 14) of the chemotypes identified.

For example, the consensus model, Formula A, suggests that a small lipophilic group such as a fluorine, chlorine, methyl or ethyl on the meta position of the left-most aryl group of the consensus scaffold could imbue a substantial activity enhancement. Initial experimentation also suggested that the right-most aryl group of the consensus scaffold might be replaced productively by a smaller group such as furan, thiophene or pyrrole.

As such, Formula A or any of the Compounds 1-32 (or 1-38) can be derivatized to establish the optimal scaffold, which can then be the basis for further compound library synthesis. With respect to Formula A or any of the Compounds 1-32 (or 1-38), this means determining the optimal atoms for a cyclic ring (e.g., any C, Y, or X of a ring being NH, N-alkyl, O, S, or the like) and/or optimal linker atom or chain (e.g., any C, O, N, Z, double bond, or the like being an amide, amine, urea, ether, or thioamide). Accordingly, any cyclic ring can be derivatized by altering a ring atom as shown in Formula A or any of the Compounds 1-32 (or 1-38) to another ring atom. Also, any linker atom or chain shown in Formula A or any of the Compounds 1-32 (or 1-38) can be altered to another linking atom or ring. For example, the synthesis can prepare analogues where Z is an amide or oxygen and X is an NH or N-alkyl). While ring groups can be substituted, they can also be increased or decreased in ring atoms, can be have the ring atoms changed to other ring atoms, or combinations thereof.

Once the scaffold is identified, such as Formula A or any of the Compounds 1-32 (or 1-38), it then becomes straightforward to synthesize a series of analogues. For example, an approximately 100 aryl-group of analogues can be prepared in a 10×10 matrix constructed using 10 different aryl groups at either end of the scaffold, where the choice of aryl group can be informed by the CoMFA model and traditional medicinal chemistry principles. Moreover, the synthesizing analogues that are expected to have appropriate drug-like characteristics (i.e., those compounds that fall within the scope of the standard Lipinski parameters) can provide optimal properties. Highly active compounds that pass through these filters can be analyzed by preliminary pharmacokinetic characterization. Finally, highly active compounds can also serve as pharmacological tools for the identification of the relevant biological targets. Thus, biotin-conjugated compounds for affinity purification or compounds containing functional groups appropriate for photo-affinity labeling can be obtained as necessary.

10.

Analogues were prepared as generally shown in FIGS. 17A-17D. Condensation of 4-Nitro-1,2-Diaminobenzene with Furaldehyde as found in the literature (Bioorg. Med. Chem. Lett. 16 (2006) 5001-5004) was utilized. To a stirred solution of 4-Nitro-1,2-diaminobenzene (1 eq, 2 g, 13.0 mmol) in pyridine (40 mL) furaldehyde (1.6 eq, 21.0 mmol, 2 g, 1.76 mL) was added. The reaction mixture was refluxed for 5 hours. After cooling to room temperature the pyridine was removed in vacuum. The residue was purified by column chromatography (silica gel, eluted with a gradient of EtOAc in Hexanes 0 to 100%) to obtain the product in sufficient purity for further elaboration. 2-(furan-2-yl)-5-nitro-1H-benzo[d]imidazole (1.5 g, 6.5 mmol, 50%) was observed as a brown solid. High resolution mass spectra (HRMS) [ESI+] were obtained using a Waters/MicroMass ICT Premier (TOF instrument). HRMS was calculated for $C_{11}H_8N_3O_3$ [M+H$^+$]: 230.0566. Found: 230.0565.

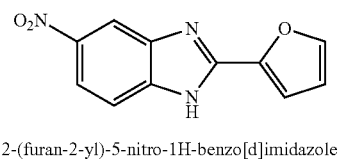 [SMILES: O=[N+]([O-])c1ccc2[nH]c(-c3ccco3)nc2c1]

2-(furan-2-yl)-5-nitro-1H-benzo[d]imidazole

For the condensation of 4-Nitro-1,2-Diaminobenzene with Thiophenecarbox-aldehyde and Pyrrole-2-carboxaldehyde a procedure found in the literature (J. Med. Chem. 51 (2008) 4899-4910) was utilized. To a stirred solution of 4-Nitro-1,2-diaminobenzene (1 eq, 2 g, 13.0 mmol) in Ethanol (200 proof, 40 mL) the aldehyde (1 eq, 13.0 mmol) and p-Benzoquinone (1 eq, 13.0 mmol, 1.4 g) was added. The reaction mixture was refluxed for 5 hours. After cooling to room temperature the Ethanol was removed in vacuum. The residue was purified by column chromatography (silica gel, eluted with a gradient of EtOAc in Hexanes 0 to 100%) to obtain the product in sufficient purity for further elaboration. 5-nitro-2-(thio)phen-2 yl)-1H-benzo[d]imidazole (1.5 g, 6.1 mmol, 47%) was observed as brown solid. HRMS calculated for $C_{11}H_8N_3O_2S$ [M+H$^+$]: 246.0337. Found: 246.0322. 5-nitro-2-(1H-pyrrol-2-yl)-1H-benzo[d]imidazole (1.32 g, 5.8 mmol, 44%) was observed as brown solid. HRMS calculated for $C_{11}H_9N_4O_2$ [M+H$^+$]: 230.0566. Found: 230.0578.

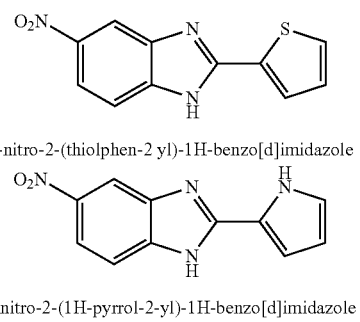

5-nitro-2-(thiolphen-2 yl)-1H-benzo[d]imidazole 5-nitro-2-(1H-pyrrol-2-yl)-1H-benzo[d]imidazole General procedure for the reduction of the nitro-compound to Amines following a known protocol (Org. Syn. Coll. 5 (1973) 346). To a stirred solution of the Nitro compound (1 eq, 5.8-6.5 mmol, 1.3-1-5 g) in a mixture of Ethanol (190 proof, 12 mL), Water (3 mL) and HCl (conc., 0.14 mL) was added Iron powder (10e eq). The reaction mixture was refluxed for 4 hours. After cooling to room temperature, the reaction mixture was filtered and washed with hot Ethanol. After removal of the solvent in vacuum the filtrate was purified by column chromatography (basic aluminium oxide, eluted with a gradient of EtOAc in Hexanes 80 to 100% followed by a gradient of MeOH in EtOAc 0 to 10%). to obtain the product in sufficient purity for further elaboration. 2-(furan-2-yl)-1H-benzo[d]imidazol-5-amine (0.823 g, 4.1 mmol, 64%) was observed as brown solid. HRMS calculated for C₁₁H₁₀N₃O [M+H⁺]: 200.0824, found: 200.0813. 2-(thiophen-2-yl)-1H-benzo[d]imidazol-5-amine (0.893 g, 4.1 mmol, 68%) was observed as brown solid. HRMS calculated for C₁₁H₁₀N₃S [M+H⁺]: 216.0595. Found: 216.0584. 2-(1H-pyrrol-2-yl)-1H-benzo[d]imidazol-5-amine (0.865 g, 4.4 mmol, 75%) was observed as brown solid. HRMS calculated for C₁₁H₁₁N₄ [M+H⁺]: 199.0964. Found: 199.0962.

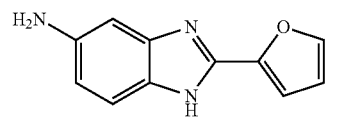

2-(furan-2-yl)-1H-benzo[d]imidazol-5-amine

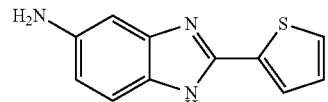

2-(thiophen-2-yl)-1H-benzo[d]imidazol-5-amine

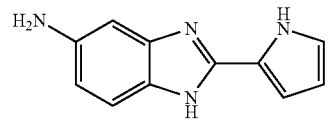

2-(1H-pyrrol-2-yl)-1H-benzo[d]imidazol-5-amine

A general procedure for the Imine formation was performed as follows. To a stirred solution of the amine (1 eq, 0.25-0.35 mmol, 50-70 mg) in MeOH (abs, 5 mL) was added the aldehyde (1.5 eq, 0.5-0.7 mmol, 70-87 mg) and dry molecular sieves (4 Å). The reaction mixture was stirred at room temperature for approximately 12 hours. After filtering off the molecular sieves, the solvent was removed in vacuum. The residue was purified by column chromatography (silica gel (pre-treated with eluent mixture), eluted with 2% NEt₃/50% EtOAc/48% Hexanes) to obtain the product in sufficient purity for biological testing. (E)-2-(furan-2-yl)-N-(3-methylbenzylidene)-1H-benzo[d]imidazol-5-amine (0.058 g, 0.19 mmol, 77%, purity: 94%) was observed as brown solid. HRMS calculated for C₁₉H₁₆N₃O [M+H⁺]: 302.1293. Found: 302.1275. (E)-N-(3-chlorobenzylidene)-2-(furan-2-yl)-1H-benzo[d]imidazol-5-amine (0.075 g, 0.23 mmol, 93%, purity: 97%) was observed as yellow solid. HRMS calculated for C₁₈H₁₃ClN₃O [M+H⁺]: 322.0747. Found: 322.0734. (E)-N-(3-fluorobenzylidene)-2-(furan-2-yl)-1H-benzo[d]imidazol-5-amine (0.050 g, 0.16 mmol, 68%, purity: 93%) was observed as yellow solid. HRMS calculated for C₁₈H₁₃FN₃O [M+H⁺]: 306.1043, found: 306.1030.

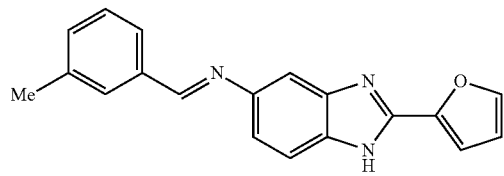

(E)-2-(furan-2-yl)-N-(3-methylbenzylidine)-1H-benzo[d]imidazol-5-amine (Compound 33)

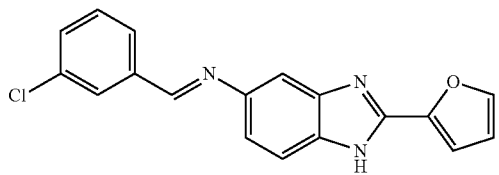

(E)-N-(3-chlorobenzylidene)-2-(furan-2-yl)-1H-benzo[d]imidazol-5-amine (Compound 36)

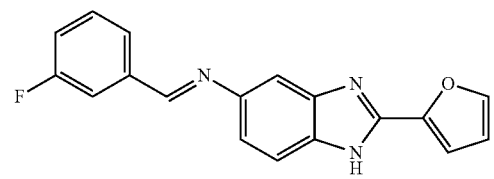

(E)-N-(3-fluorobenzylidene)-2-(furan-2-yl)-1H-benzo[d]imidazol-5-amine (Compound 37)

A general procedure for the reductive amination was performed as follows. To a stirred solution of the amine (1 eq, 0.25 mmol, 50 mg) in MeCN (5 mL) was added the aldehyde (1.6 eq, 0.375 mmol, 45-53 mg) followed by NaBH(OAc)₃ (2.5 eq). The reaction mixture was stirred at room temperature for approximately 12 hours. Unreacted NaBH(OAc)₃ was quenched by the addition of MeOH (2 mL). The reaction mixture was concentrated in vacuum. The residue was purified by preparative thin layer chromatography (silica gel, eluted with 75% EtOAc in Hexanes) to obtain the product in sufficient purity for biological testing. 2-(furan-2-yl)-N-(3-methylbenzyl)-1H-benzo[d]imidazol-5-amine (0.037 g, 0.12 mmol, 35%, purity: 98%) was observed as brown solid. HRMS calculated for C₁₉H₁₈N₃O [M+H⁺]: 304.1450. Found: 304.1435. N-(3-chlorobenzyl)-2-(furan-2-yl)-1H-benzo[d]imidazol-5-amine (0.053 g, 0.16 mmol, 65%, purity: 91%) was observed as brown solid. HRMS calculated for C₁₈H₁₅ClN₃O [M+H⁺]: 324.0904. Found: 324.0912. N-(3-fluorobenzyl)-2-(furan-2-yl)-1H-benzo[d]imidazol-5-amine (0.041 g, 0.16 mmol, 47%, purity: 100%) was observed as orange solid. HRMS calculated for C₁₈H₁₅FN₃O [M+H⁺]: 308.1199. Found: 308.1186. N-(3-methylbenzyl)-2-(1H-pyrrol-2-yl)-1H-benzo[d]imidazol-5-amine (0.039 g, 0.13 mmol, 52%, purity: 96%) was observed as brown solid. HRMS calculated for C₁₉H₁₉N₄ [M+H⁺]: 303.1610. Found: 303.1591. N-(3-chlorobenzyl)-2-(1H-pyrrol-2-yl)-1H-benzo[d]imidazol-5-amine (0.035 g, 0.11 mmol, 43%, purity: 95%) was observed as brown solid. HRMS calculated for C₁₈H₁₆ClN₄ [M+H⁺]: 323.1063. Found: 323.1030.

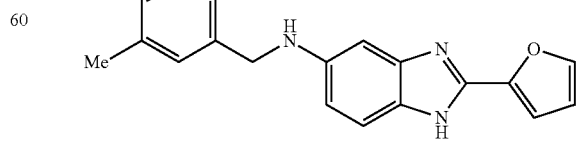

2-(furan-2-yl)-N-(3-methylbenzyl)-1H-benzo[d]imidazol-5-amine

-continued

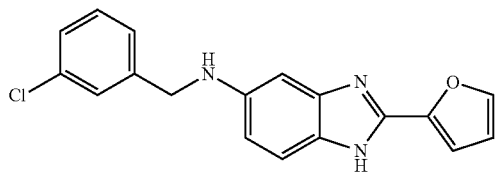

N-(3-chlorobenzyl)-2-(furan-2-yl)-1H-benzo[d]imidazol-5-amine
(Compound 38)

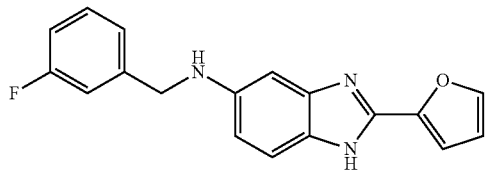

N-(3-fluorobenzyl)-2-(furan-2-yl)-1H-benzo[d]imidazol-5-amine
(Compound 35)

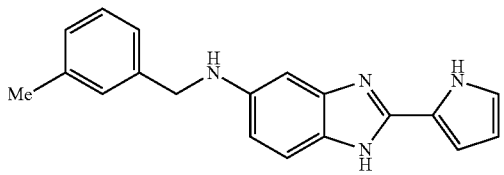

N-(3-methylbenzyl)-2-(1H-pyrrol-2-yl)-1H-benzo[d]imidazol-5-amine

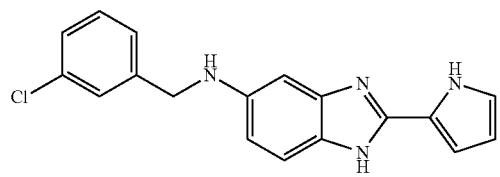

N-(3-chlorobenzyl)-2-(1H-pyrrol-2-yll)-1H-benzo[d]imidazol-5-amine

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references or citations of publications or presentations (e.g., patents, published patent applications, journal articles, abstracts, posters, and the like) disclosed herein are incorporated into this provisional patent application by specific reference in their entirety.

The invention claimed is:

1. A pharmaceutical composition comprising Compound 17

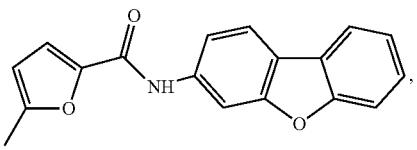 [SMILES: Cc1ccc(C(=O)Nc2ccc3c(c2)oc2ccccc23)o1]

or a pharmaceutically acceptable salt thereof; and a pharmaceutically acceptable carrier containing the compound.

2. The composition of claim 1, wherein the pharmaceutically acceptable carrier is for oral, systemic, transdermal, intranasal, suppository, parenteral, intramuscular, intravenous, or subcutaneous administration.

3. The composition of claim 1, wherein the compound is present in a therapeutically effective amount.

4. The composition of claim 1, wherein the compound is present in a therapeutically effective amount for enhancing production of BRCA1.

5. A method of treating or inhibiting breast or ovarian cancer comprising administering to a subject in need thereof a therapeutically effective amount of Compound 17

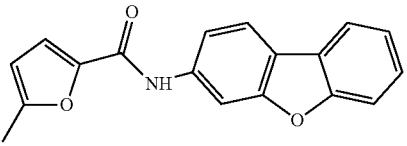 [SMILES: Cc1ccc(C(=O)Nc2ccc3c(c2)oc2ccccc23)o1]

6. The method of claim 1, wherein the method inhibits the growth or propagation of breast or ovarian cancer cells.

7. The method of claim 5, wherein BRCA1 production is increased in the subject compared to BRCA1 production in the subject prior to being administered the compound.

8. A method of increasing BRCA1 production in breast or ovarian cancer cells comprising administering to a subject in need thereof a therapeutically effective amount of Compound 17

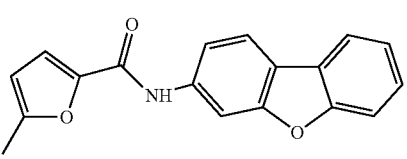 [SMILES: Cc1ccc(C(=O)Nc2ccc3c(c2)oc2ccccc23)o1]

9. The method of claim 8, wherein the method inhibits the growth of the breast or ovarian cancer cells.

* * * * *

UNITED STATES PATENT AND TRADEMARK OFFICE
CERTIFICATE OF CORRECTION

PATENT NO. : 8,362,072 B2  
APPLICATION NO. : 13/525831  
DATED : January 29, 2013  
INVENTOR(S) : Jensen et al.

Page 1 of 1

It is certified that error appears in the above-identified patent and that said Letters Patent is hereby corrected as shown below:

In the Claims:  
In column 46, Claim 6, line 36, please delete "claim 1"

In the Claims:  
In column 46, Claim 6, line 36, please insert --claim 5--

In the Claims:  
In column 46, Claim 8, line 44, please delete "17"

In the Claims:  
In column 46, Claim 8, line 44, please insert --17.--

Signed and Sealed this  
Nineteenth Day of March, 2013

Teresa Stanek Rea  
*Acting Director of the United States Patent and Trademark Office*